US007081343B2

(12) United States Patent
Chen et al.

(10) Patent No.: US 7,081,343 B2
(45) Date of Patent: Jul. 25, 2006

(54) METHODS FOR IDENTIFYING MODULATORS OF NF-KB ACTIVITY

(75) Inventors: Lin-feng Chen, San Francisco, CA (US); Wolfgang Fischle, Charlottesville, VA (US); Eric M. Verdin, San Francisco, CA (US); Warner C. Greene, Hillsborough, CA (US)

(73) Assignee: The Regents of the University of California, Oakland, CA (US)

( * ) Notice: Subject to any disclaimer, the term of this patent is extended or adjusted under 35 U.S.C. 154(b) by 85 days.

(21) Appl. No.: 09/884,875

(22) Filed: Jun. 18, 2001

(65) Prior Publication Data
US 2002/0193284 A1     Dec. 19, 2002

(51) Int. Cl.
G01N 33/53    (2006.01)
C12Q 1/34     (2006.01)
C12Q 1/02     (2006.01)
(52) U.S. Cl. ............................ 435/7.1; 435/18; 435/29
(58) Field of Classification Search ................ 435/6, 435/29, 4, 320.1, 440, 325, 252.3, 7.1; 536/23.1
See application file for complete search history.

(56) References Cited

U.S. PATENT DOCUMENTS

| 5,804,374 A | 9/1998 | Baltimore et al. |
| 6,037,133 A | 3/2000 | Li |
| 6,150,090 A | 11/2000 | Baltimore et al. |
| 6,242,253 B1* | 6/2001 | Karin et al. ................. 435/325 |
| 6,242,254 B1 | 6/2001 | Efrat |
| 6,410,516 B1 | 6/2002 | Baltimore et al. |
| 6,416,959 B1* | 7/2002 | Giuliano et al. ............. 435/7.2 |

OTHER PUBLICATIONS

Traenckner, et al. The EMBO Journal, vol. 13, No. 22, pp. 5433-5441, 1994.*
Ganchi et al. Molecular Biology of the Cell, 1992, vol. 3, pp. 1339-1352.*
Baldwin, "The NF-κB and IκB proteins: New discoveries and insights", *Annu. Rev. Immunol.* (1996) vol. 14: 649-683.
Bird. "Activation of nuclear transcription factor NF-κB by interleukin-1 is accompanied by casein kinase II-mediated phosphorylation of the p65 subunit", *J. Biol. Chem.*, (1997) Vol. 272: 32606-32612.
Boyes, et al. Regulation of activity of the transcription factor GATA-1 by acetylation, *Nature*, (1998) vol. 396: 594-598.
Chakravarti, et al. "A viral mechanism for inhibition of p300 and PCAF acetyltransferase activity", *Cell*, (1999) vol. 96: 393-403.
Cress, et al. "Histone deacetylases, transcriptional control, and cancer", *J. Cell Physiol.*, (2000) vol. 184: 1-16.
Deloukas, et al. "Genomic organization of the gene encoding the p65 subunit of NF-κB: Multiple variants of the p65 protein may be generated by alternative splicing", *Hum. Mol. Genet.*, (1993) vol. 2 1895-1900.
Gerritsen, et al. "Creb-binding protein/p300 are transcriptional coactivators of p65", *Proc. Natl. Acad. Sci. USA*, (1997) vol. 94: 2927-2932.
Ghosh, et al. NF-κB and rel proteins: Evolutionarily conserved mediators of immune responses, *Annu. Rev. Immunol.* (1998) vol. 16: 225-260.
Hamamori, et al. "Regulation of histone acetyltransferases p300 and PCAF by the bHLH protein twist and adenoviral on oncoprotein E1A", *Cell*, (1999) vol. 96: 405-413.
Hottiger. "Modulation of cytokine-induced HIV gene expression by competitive binding of transcription factors to the coactivator p300", *EMBO J.*, (1998) vol. 17: 3124-3134.
Imhof, et al. "Transcription: Gene control by targeted histone acetylation", *Curr. Biol.*, (1998) vol. 8, 422-424.
Jacobs, et al. "Structure of an I-kappa-B-alpha/NF-κB complex", *Cell*, (1998) vol. 95(6) 749-758.
Karin. How NF-κB is activated: The role of the I-κB kinase (IKK) complex, *Oncogene*, (1999) vol. 18: 6867-6874.
Kouzarides. "Acetylation: A regulatory modification to rival phosphorylation?", *EMBO J.*, (2000) vol. 19: 1176-1179.
Kraus, et al. "Biochemical analysis of distinct activation functions in p300 that enhance transcription initiation with chromatin templates", *Mol. Cell. Bio.*, (1999) vol. 19: 8123-8135.
Kuo, et al. "Roles of histone acetyltransferases and deacetylases in gene regulation", *Bioessays*, (1998) vol. 20: 615-626.
Lyle, et al. "An alternatively spliced transcript, p65 delta 2, of the gene encoding the p5 subunit of the transcription factor NF-κB", *Gene*, (1994) vol. 138: 265-266.
Madge, et al. "A phosphatidylinositol 3-kinase/Akt pathway, activated by tumor necrosis factor or interleukin-1, inhibits apoptosis but does not activate NF-κB in human endothelial cells", *J. Biol. Chem.*, (2000) vol. 275: 15458-15465.
Martínez-Balbás, et al. "Regulation of E2F1 activity by acetylation", *Embo. J.*, (2000) vol. 19: 662-671.
May, et al. "Rel/NF-κB and I-κproteins: An overview", *Sem. Cancer Biol.* (1997) vol. 8: 63-73.
May, et al. "Signal transduction through NF-κB", *Immunol. Today*, (1998) vol. 19(2): 80-88.
Ng, et al. "Histone deacetylases: Silencers for hire", *TIBS*, (2000) vol. 25: 121-126.
Perkins, et al. "Regulation of NF-κB by cyclin-dependent kinases associated with the p300 coactivator", *Science*, (1997) vol. 275: 523-527.

(Continued)

*Primary Examiner*—Celine Qian
*Assistant Examiner*—Jennifer Dunston
(74) *Attorney, Agent, or Firm*—Carol L. Francis; Edward J. Baba; Bozicevic, Field & Francis LLP

(57) ABSTRACT

The present invention provides methods for identification of agents that modulate NF-κB activity through modulation of the acetylation and deacetylation of the RelA subunit of NF-κB.

18 Claims, 7 Drawing Sheets

OTHER PUBLICATIONS

Ruben, et al. "Isolation of a rel-related human cDNA that potentially encodes the 65-kD subunit of NF-$_\kappa$B", *Science*, (1991) vol. 251: 1490-1493.

Rundlett, et al. "HDA1 and RPD3 are members of distinct yeast histone deacetylase complexes that regulate silencing and transcription", *Proc. Natl. Acad. Sci. USA*, (1996) vol. 93: 14503-14508.

Sen, et al. "Multiple nuclear factors interact with the immunoglobulin enhancer sequences", *Cell*, (1986) vol. 46: 705-716.

Sakurai. "I-$_\kappa$B kinases phosphorylate NF-$_\kappa$B p65 subunit on serine 536 in the transactivation domain", *J. Biol. Chem.*, (1999) vol. 274: 30353-30356.

Sheppard, et al. "Transcriptional activation by NF-$_\kappa$B requires multiple coactivators", *Mol. Cell. Biol.*, (1999) vol. 19: 6367-6378.

Sterner, et al. "Acetylation of histones and transcription-related factors", *Microbiol. Mol. Biol. Rev.*, (2000) vol. 64: 435-459.

Sun, et al. "NF-$_\kappa$B controls expression of inhibitor I-$_\kappa$Bβ: Evidence for an inducible autoregulatory pathway", *Science*, (1993) vol. 259: 1912-1915.

Taunton, et al. "A mammalian histone deacetylase related to the yeast transcriptional regulator Rpd3p", *Science*, (1996) vol. 272: 408-411.

Wang. "Tumor necrosis factor β-induced phosphorylation of ReIA/p65 on Ser$^{259}$ is controlled by casein kinase II", *J. Biol. Chem.*, (2000) vol. 275: 32592-32597.

Yoshida, et al. "Trichostatin and leptomycin: Inhibition of histone deactylation and signal-dependent nuclear export", *Ann N.Y. Acad. Sci.*, (1999) vol. 886: 23-36.

Zhong, et al. "Phosphorylation of NF-$_\kappa$B p65 by PKA stimulates transcriptional activity by promoting a novel bivalent interaction with the coactivator CBP/p300", *Mol. Cell*, (1998) vol. 1: 661-671.

Chen, Lin-feng et al., "*Duration of Nuclear NF-$_\kappa$B Action Regulated by Reversible Acetylation*", Science 293 (5535) 1653-1657 (Aug. 2001).

\* cited by examiner

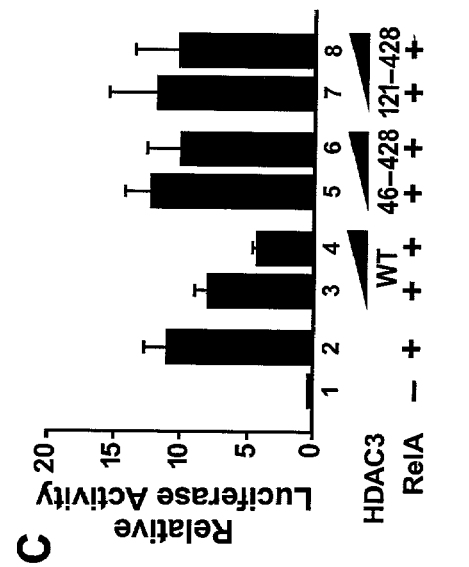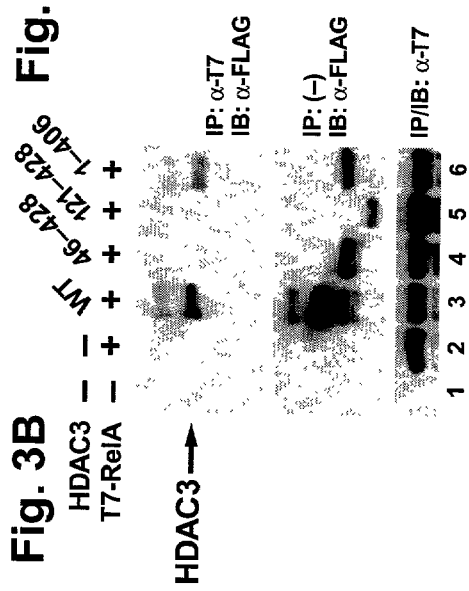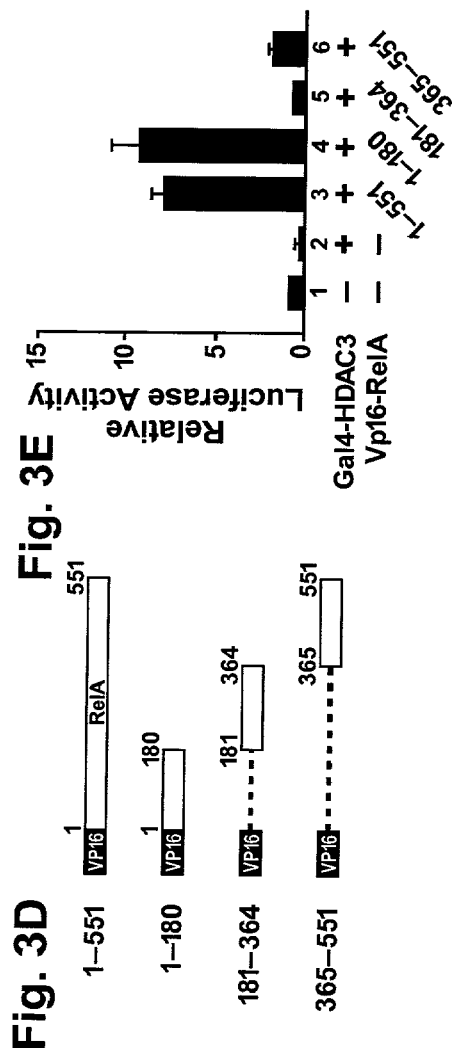

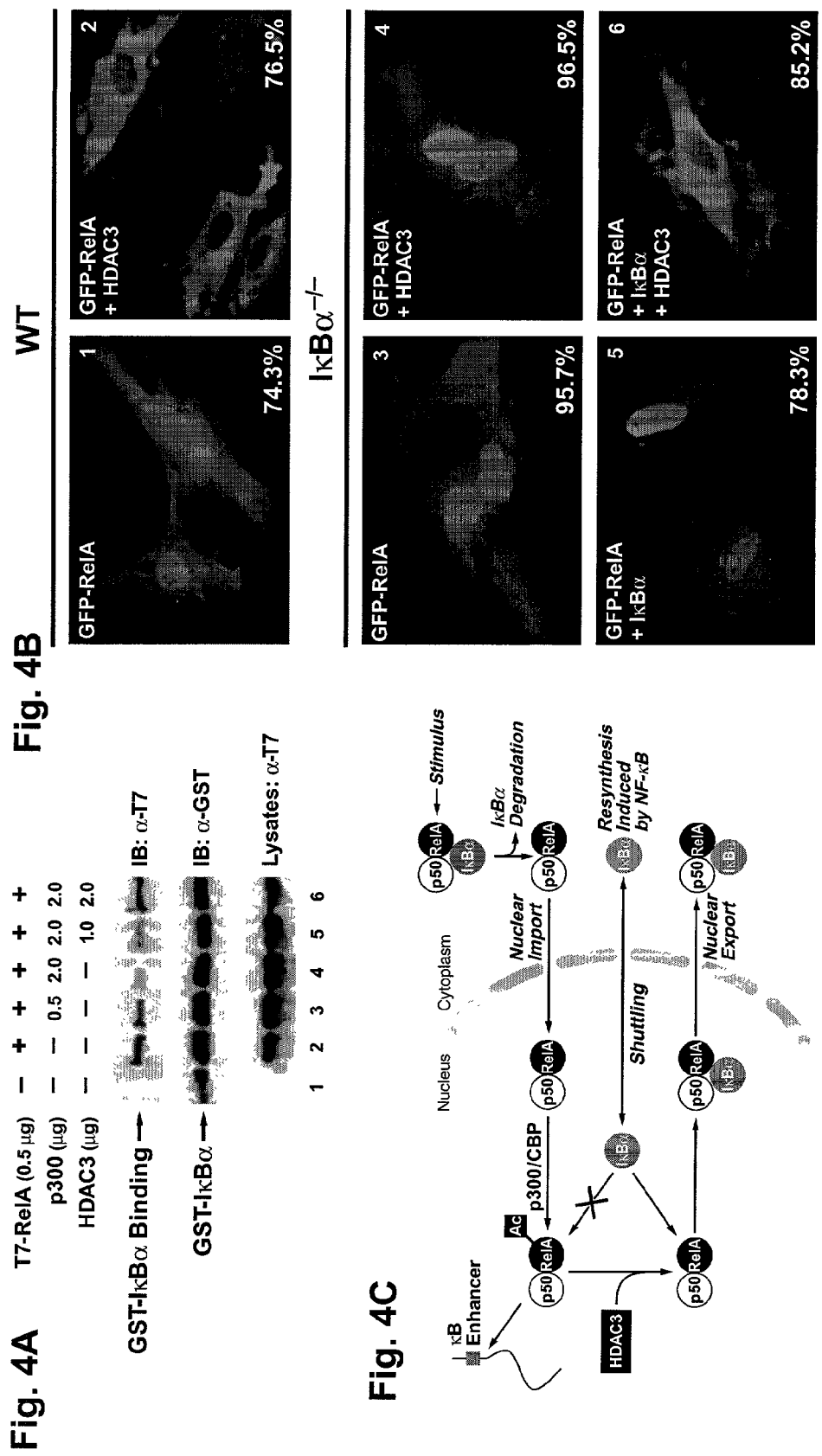

METHODS FOR IDENTIFYING MODULATORS OF NF-κB ACTIVITY

FIELD OF THE INVENTION

The field of the invention is in immunology and provides methods for screening agents that inhibit transcription by NF-κB in a host by promoting deacetylation of RelA. NF-κB acts as a DNA-binding protein in a wide variety of cells.

BACKGROUND OF THE INVENTION

NF-κB, a heterodimer of the proteins p50 and RelA, is an inducible eukaryotic transcription factor complex that is broadly expressed and plays a pivotal role in regulating multiple biological responses, such as the inflammatory and immune responses in mammalian cells. See, Baldwin, Jr., *Annu. Rev. Immunol.* 14:649–683 (1996) and Ghosh, S. et al., *Annu. Rev. Immunol.* 16:225–260 (1998). NF-κB binds to regulatory regions of genes, termed enhancers, that increase the expression of these genes thereby exerting important effects on inflammatory, immune and anti-apoptotic responses. Activation of NF-κB is implicated in a variety of chronic inflammatory diseases. In addition, the long terminal repeat (LTR) of HIV is subject to activation by NF-κB, a response that can lead to heightened levels of viral replication.

NF-κB was first identified as a constitutively expressed protein that bound to a specific decameric DNA sequence (5'-ggg act ttc c-3' SEQ ID NO:1), within the intronic enhancer of the immunoglobulin kappa light chain in mature B- and plasma cells, but not pre B-cells (Sen et al. (1986) *Cell* 46:705–716). Later, it was demonstrated that the DNA binding activity of NF-κB is induced in most cells following exposure to a variety of exogenously applied stimuli, and that this activation occurs independently of de novo protein synthesis. NF-κB binds to specific sites on DNA (referred to as κB sites, and having the general consensus sequence: 5'-ggg rnn tyc c-3' (SEQ ID NO:2), where R is a purine, and Y is a pyrimidine). These κB sites have been identified in promoters and enhancers of a large number of inducible NF-κB genes. For reviews see, e.g., May et al., *Sem. Cancer Biol.* 8:63–73 (1997); and May et al., *Immunol. Today* 19(2):80–88 (1998).

The prototypical NF-κB complex, which corresponds to a heterodimer of p50 and RelA subunits, is kept in an inactive form and sequestered in the cytoplasm by a family of inhibitory proteins termed the IκBs, which includes IκBα. Upon exposure to a wide variety of stimuli, for example proinflammatory cytokines like tumor necrosis factor α (TNF-α), and interleukin 1 (IL-1), IκBα is phosphorylated. This event, mediated by a macromolecular IκB kinase complex (IKK) (Karin, M., *Oncogene* 18:6867–6874 (1999)), triggers the rapid ubiquitination and subsequent degradation of this inhibitor by the 26S proteasome complex. The unmasking of the nuclear localization signal in the RelA component of the p50/RelA NF-κB heterodimer allows its rapid translocation into the nucleus, where it engages cognate κB sites and activates transcription of various target genes.

Transcriptional activation by NF-κB principally reflects the action of its RelA subunit, which contains an active C-terminal transcriptional activation domain. In contrast, the p50 subunit principally plays a role in DNA binding. Overall transcriptional activity of the RelA subunit is also regulated by casein kinase II- and IKK-mediated phosphorylation of serine residues present in the C-terminal activation domain of RelA. See, for example, Sakurai, H., *J. Biol. Chem.* 274:30353–30356 (1999), Wang, D., *J. Biol. Chem.* 275:32592–32597 (2000), and Bird, T. A., *J. Biol. Chem.* 272:32606–32612 (1997).

Binding of NF-κB to DNA promotes the recruitment of such co-activators as p300 or CBP (cyclic AMP Response Element Binding Protein (CREB) Binding Protein) and P/CAF that participate in the transcriptional activation of target genes. See, Perkins, N. D. et al., *Science* 275:523–527 (1997), Hottiger, M. O., *EMBO J.* 17:3124–3134 (1998), and Sheppard, K. A. et al., *Mol. Cell. Biol.* 19:6367–6378 (1999). Phosphorylation of the N-terminal portion of the RelA subunit by protein kinase A facilitates its assembly with CBP/p300 (Zhong, H. et al., *Mol. Cell* 1:661–671 (1998)). Both CBP and p300 exhibit histone acetyltransferase activity, which has been implicated in the control of gene expression. This action involves both acetylation of core histones that lead to changes in chromatin structure, and direct acetylation of select host transcription factors like p53, GATA-1 and E2F, where acetylation alters the biological function of the factors. See, for example, Imhof, I. and Wolffe, A. P., *Curr. Biol.* 8:422–424 (1998); Sterner, D. E. and Berger, S. L., *Microbiol. Mol. Biol. Rev.* 64:435–459 (2000); and Kouzarides, M. T., *EMBO J.* 19:1176–1179 (2000).

Although the biochemical steps underlying IκB degradation and NF-κB activation are relatively well understood, much less is known about how the cell re-establishes control over the powerfully active nuclear NF-κB complexes once they are expressed in the nucleus.

Histones are proteins found in the nucleus that play a major role in regulating gene expression by modifying chromatin structure. See, Imhof, A. and Wolffe, A. P., *Curr. Biol.* 8:422–424 (1998). Histones are acetylated and deacetylated in vivo. These opposing processes are regulated by two complementary groups of enzymes, the histone acetyltransferases (HATs) and histone deacetylases (HDACs). Eight different HDACs (HDAC 1–8) have now been identified in mammalian cells. See, Cress, W. D. and Seto, E., *J. Cell Physiol.* 184:1–16 (2000). Based on their primary structure, these HDACs have been divided into two classes; the class I HDACs include HDAC 1, 2, 3 and 8, which share homology with a yeast transcriptional repressor, RPD3 (Taunton, J. et al., *Science* 272:408–411 (1996)), and the class II HDACs including HDAC 4, 5, 6 and 7, which display similarity to another yeast deacetylase, HDA1 (Rundlett, S. E. et al., *Proc. Natl. Acad. Sci. USA* 93:14503–14508 (1996)). Each of the HDACs contains a conserved catalytic domain that mediates deacetylation of histones (Ng, H. H. and Bird, A., *TIBS* 25:121–126 (2000)). In general, acetylation of histones by the HATs promotes nucleosome rearrangement and transcriptional activation. Conversely, deacetylation of histones by the HDACs promotes nucleosome assembly and transcriptional repression. See, Kouzarides, M. T., *EMBO. J.* 19:1176–1179 (2000) and Kuo, H. and Allis, C. D., *Bioessays*, 20:615–626 (1998). In addition, it is known that trichostatin A (TSA) is a specific inhibitor of the HDACs. See, Yoshida, M. and Horinouchi, S., *Ann N.Y. Acad. Sci.* 886:23–36 (1999).

Since NF-κB plays a key role in regulating both inflammatory and immune responses in mammalian cells, as well as contributing to cancer cell growth and increased replication of various viruses like HIV-1, the development of agents that impair NF-κB activation or function could have important therapeutic applications. The present invention describes a novel approach to the regulation of nuclear NF-κB activity taking advantage of the recent observation that nuclear NF-κB action is regulated by reversible acetylation.

There is a need for compositions and methods to modulate NF-κB activity, particularly agents that modulate NF-κB activity through a mechanism or pathway different from the NE-κB modulating agents currently available. Providing such agents expands the scope of methods for treating conditions associated with dysregulation of NF-κB activity, thus ultimately providing the clinician and the patient with alternative therapies. Thus, there is a need for methods for identifying agents that can modulate NF-κB activity through, for example, a pathway other than that involving regulation of interaction with IκBα and its components, or other extranuclear pathway. The present invention addresses this need.

SUMMARY OF THE INVENTION

The present invention provides methods for identification of agents that modulate NF-κB activity through modulation of the acetylation and deacetylation of the RelA subunit of NF-κB.

These and other objects, advantages, and features of the invention will become apparent to those persons skilled in the art upon reading the details of the subject methods as more fully described below.

BRIEF DESCRIPTION OF THE DRAWINGS

FIG. 2A is a photograph of a gel, demonstrating that overexpressed RelA is acetylated in vivo and deacetylated by HDAC3, but not HDAC1.

FIG. 2B is a photograph of a gel showing stimulus-coupled (TNF-α) acetylation of endogenous RelA.

FIG. 2C is a photograph of a gel showing signal-coupled acetylation of RelA by p300.

FIG. 2D is a photograph of a gel that shows co-expression of p300 or CBP with RelA produces dose-related acetylation of T7-RelA, while P/CAF failed to exert comparable effects.

FIG. 3A is a schematic showing where N- and C-terminal deletions were made in HDAC3 to map regions potentially required for interaction with RelA.

FIG. 3B is a photograph of a gel showing that RelA and HDAC co-immunoprecipitate and that the N-terminal region (amino acids 1–45) of HDAC3 is required for this interaction FIG. 3C is a bar graph showing the relative luciferase activity when the wild-type and N-terminal deletions of HDAC3 are contacted with RelA.

FIG. 3D is a schematic illustrating deletions made in RelA for testing in the mammalian 2 hybrid interaction assay.

FIG. 3E is a bar graph showing that the N-terminal region of RelA (amino acids 1–180) are sufficient for the assembly of RelA with HDAC3.

FIG. 4A is a photograph of a gel showing that deacetylated RelA displays greater IκBα binding activity than acetylated forms of RelA.

FIG. 4B is a series of six photographs showing that HDAC3 does not stimulate RelA nuclear export in IκBα-deficient mouse embryo fibroblasts.

FIG. 4C is a summary schematic showing nuclear RelA is acetylated by p300/CBP which prevents its binding to newly synthesized IκBα inhibition, which shuttles in and out of the nucleus. However, following deacetylation of RelA by HDAC3, RelA is readily recognized by IκBα, which mediates nuclear export of the RelA containing complex, thus terminating the NF-κB-mediated transcriptional response and replenishing the cytoplasmic stores of the latent NF-κB-IκB complex.

DETAILED DESCRIPTION OF THE INVENTION

Figure 1A:
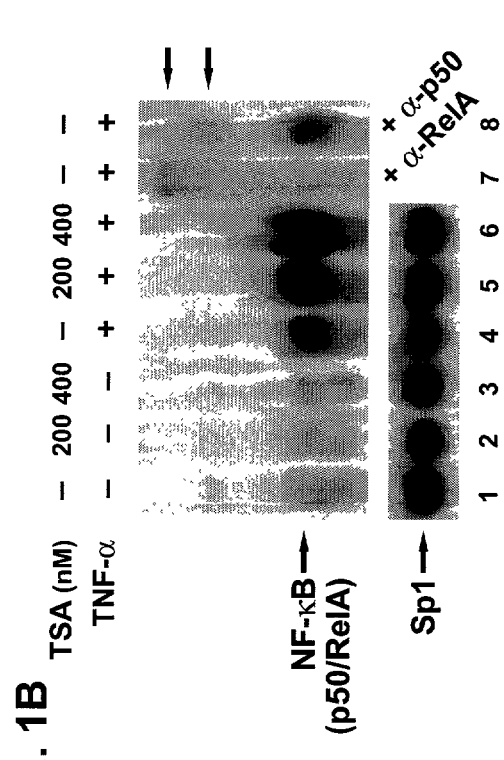
FIG. 1A is a bar graph showing the increased activity of a transfected κB-luciferase reporter plasmid in the presence of Trichostatin A (TSA) and TNF-α.

Before the present methods are described, it is to be understood that this invention is not limited to the particular methods described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural references unless the context clearly dictates otherwise. Thus, for example, reference to "a RelA subunit" includes a plurality of such RelA subunits and reference to "the cell" includes reference to one or more cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided might be different from the actual publication dates, which may need to be independently confirmed.

Definitions

"Nuclear factor κB (NF-κB)" as used herein, refers to a heterodimeric complex of the protein subunits p50 and RelA. In most of the wide variety of cells that express NF-κB, this factor is retained in the cytoplasm in an inactive form complexed with an inhibitor (IκBα). Once released from the inhibitor, NF-κB enters the nucleus and binds to κB DNA enhancers to facilitate transcriptional activation of various NF-κB inducible genes.

"RelA" formerly called p65, is the subunit of NF-κB that, as discovered by the present inventors, is a substrate for acetylation by p300 and CBP, and deacetylation by HDAC3. When RelA is deacetylated in vivo, it is able to bind to IκBα, which in turn leads to nuclear export, thus serving to decrease the level of active NF-κB in the nucleus and decreasing NF-κB-mediated transcriptional activity.

An "agent that deacetylates RelA" as used herein, describes any molecule, e.g., synthetic or natural organic or inorganic compound, protein or pharmaceutical, that can effect deacetylation of the RelA subunit of NF-κB, as described herein.

By "isolated" is meant that the sample is enriched for the substance (e.g., nucleic acid or polypeptide) or obtained in substantial purity, generally as other than an untreated cell extract. Usually, the substance (e.g., nucleic acid or polypeptide) is obtained substantially free of other cell components that naturally accompany the substance, the substance being obtained in generally at least about 50%, usually at least about 90% pure. Isolated substances include recombinant and naturally occurring substances.

Overview

The activity of the nuclear transcription factor, NF-κB (a heterodimer composed of p50 and RelA) is tightly regulated in the cytoplasm by its interaction with a family of cytoplasmic inhibitory proteins, IκB. The IκBs prevent the nuclear transport of NF-κB by masking the nuclear localization signal present in RelA. Following signal-coupled degradation of IκBα, the nuclear localization signal in RelA is unmasked, allowing NF-κB to be rapidly transported into the nucleus, where it binds to the DNA at κB sites. DNA binding by the NF-κB leads to the recruitment of the p300/CBP and P/CAF co-activators, which participate in activation of target gene transcription. Among the many target genes activated by NF-κB is the IκBα gene. The active NF-κB remains in the nucleus until the RelA subunit is deacetylated by HDAC3. Deacetylated, but not acetylated forms of RelA are effectively bound by IκBα. The binding of IκBα to deacetylated RelA promotes nuclear export of the RelA containing transcription factor complex, thereby terminating the NF-κB-mediated transcriptional response.

Until the present invention, the regulatory mechanism for control of nuclear NF-κB transcriptional activity was unknown. Thus, there are no methods or agents available that can modulate (e.g., increase or decrease) NF-κB transcriptional activity once it reaches the nucleus. As a result, if efforts to modulate the interaction between IκBα and NF-κB fail, then modulation of the acetylation/deacetylation of NF-κB affords an alternative pathway to modulate transcription.

The present invention is based on the discovery of a complementary control mechanism in the nucleus, involving reversible acetylation of the RelA subunit of NFκB. The inventors discovered that RelA, the transcriptionally active component of the NF-κB heterodimer, is acetylated by p300 and CBP. The inventors further show that RelA is selectively deacetylated by histone deacetylase 3 (HDAC3). This deacetylation reaction promotes IκBα binding and nuclear export of the NF-κB complex. Accordingly, the NF-κB transcriptional response is terminated and the depleted cytoplasmic pool of latent NF-κB/IκBα is replenished. Deacetylation of RelA thus forms an intra-nuclear molecular switch for regulating NF-κB action.

Reversible acetylation plays a key role in regulating NF-κB activity. For example, HDAC3, but not HDAC1, 2, 4, 5 or 6, selectively inhibits TNF-α activation of NF-κB-dependent luciferase activity. Further, the inventors have shown that HDAC3-mediated deacetylation of RelA stimulates IκBα dependent nuclear export or this factor via a leptomycin-B sensitive pathway. The inventors have thus discovered that RelA is a non-histone substrate for HDAC3 that links deacetylation to the nuclear export of a eukaryotic transcription factor.

This unique action of HDAC3 involving a non-histone cellular substrate ensures a high level of control over the powerful RelA transcription factor, and helps to limit the stimulus-coupled transcriptional response. Deacetylated forms of NF-κB become substrates for IκBα binding and CRM-1 dependent nuclear export, which appears dependent on the nuclear export signal present in IκBα. These effects thus oppose the stimulus-induced degradation of IκBα and translocation of NF-κB complexes into the nucleus. Nuclear export of NF-κB triggered by deacetylation complements the negative feedback loop produced by NF-κB activation of IκBα synthesis, which serves to restore the depleted cytoplasmic pool of this NF-κB inhibitor. See, for example, Sun, S. C. et al., *Science* 259:1912–1915 (1993), Brown, K. et al., *Proc. Natl. Acad. Sci.* USA 90:2532–2536 (1993), and Beg, A. A. et al., *Mol. Cell. Biol.* 13:3301–3310 (1993).

The unique action of HDAC3 on RelA also provides a mechanism to modulate the action of the NF-κB transcription factor. For example, agents that promote deacetylation of RelA will serve to decrease NF-κB transcriptional activity, which in turn will serve to down-regulate those genes that are positively regulated by NF-κB activity. Such deacetylation and export provides a unique mechanism to limit nuclear NF-κB action in stimulated cells.

Similarly, the action of p300 and CBP in acetylation of RelA provides a mechanism to modulate the NF-κB transcription factor. For example, agents that promote acetylation of RelA will serve to increase NF-κB transcriptional activity by preventing IκBα binding. In turn, those genes that are positively regulated by NF-κB will be up-regulated in activity. Acetylation of RelA thus provides a mechanism to increase NF-κB activity in cells. Increasing NF-κB activity is of interest in situations of immunodeficiency where NF-κB induction is low, and thus increasing NF-κB activity would be desirable.

The screening assays of the invention are thus based on the discovery of these mechanisms that modulate NF-κB activity. It was discovered that HDAC3 selectively inhibits TNF-α activation of a κB-luciferase reporter, and further that HDAC3 assembles with, and mediates deacetylation of RelA. This action of HDAC3 allows IκBα binding and in turn, export of the NF-κB complex out of the nucleus and into the cytoplasm. The resulting nuclear export of this factor is a strategy employed within the cell to limit the transcriptional activity of signal induced nuclear NF-κB complexes. These results provide evidence that pivotally links deacetylation to the docking of a specific inhibitor and export of a nuclear eukaryotic transcription factor-inhibitor complex.

Screening Assays

The present invention provides screening assays to identify agents that modulate an activity of a component of a NF-κB transcription pathway, e.g., a component of a pathway whose end product is increased transcription of cellular target genes. The screening assays are designed to identify agents that are useful as therapeutic agents for modulating NF-κB transcriptional activity, e.g., by decreasing the level of NF-κB-mediated transcription (and thereby reduce inflammation, increase apoptosis, and the like) or by increasing the level of NF-κB-mediated transcription. Situations of immune deficiency due to low NF-κB induction is an example of when increases in NF-κB activity would be desirable. Both cell-based and cell-free assays are provided.

In some embodiments, the screening assays are cell-free screening assays. In these embodiments, the methods generally involve contacting isolated NF-κB comprising RelA, or an isolated RelA protein or fragment thereof susceptible to de/acetylation with a test agent, and determining the effect, if any, on the acetylation state of RelA. Components that are suitable for use in a cell-free screening assay include, but are not limited to HDAC3, deacetylated RelA, acetylated RelA, NF-κB, and the like, as well as fragments of these components that retain activity, e.g., a fragment of HDAC3 that retains activity in deacetylation of RelA, a fragment of RelA that is susceptible to de/acetylation, and the like.

In other embodiments, the methods provide cell-based assays. In these embodiments, the methods generally involve contacting a host cell, which produces an activated NF-κB and a candidate agent, and determining the effect, if any, on the amount of transcription in the presence and absence of a candidate agent and the effects of such agents on the acetylation status of RelA.

Exemplary candidate agents suitable for screening, as well as exemplary screening methods within the scope of the invention, will now be described.

Identifying Agents Suitable for Modulating NF-κB Activity

Of particular interest in the present invention is the identification of agents having activity in affecting the transcriptional activity or function of NF-κB through modulation of RelA acetylation. In general, agents of interest are those that: 1) inhibit NF-κB activity, e.g., by promoting deacetylation of the RelA subunit; 2) stimulate activity of HDAC3 or the interaction of its deacetylation activities with the RelA subunit of NF-κB; and/or 3) enhancing or mimicking HDAC3 activity by deacetylation of RelA. Such agents are candidates for development as novel anti-inflammatory agents or new treatments for clinical situations where overstimulation by NF-κB occurs (chronic inflammatory states, autoimmunity, etc.). Also of interest are agents that increase NF-κB activity, e.g., by acetylation of RelA, by maintaining RelA in its acetylated state, and/or by inhibiting the activity of HDAC3 on RelA. Of particular interest are screening assays for agents that have a low toxicity for human cells and/or high specificity for RelA. Such agents can find application in various forms of immunodeficiency.

The term "agent" as used herein describes any molecule, e.g. protein or pharmaceutical, with the capability of altering NF-κB activity according to the invention. Generally, pluralities of assay mixtures are run in parallel with different agent concentrations to detect differential responses to the various concentrations. Typically, one of these concentrations serves as a negative control, i.e., at zero concentration or below the level of detection.

Candidate Agents

Candidate agents encompass numerous chemical classes, though typically they are organic molecules, and are generally small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, pheromones, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs.

Screening of Candidate Agents

In general, an agent of interest is one that modulates transcriptional activity of NF-κB by modulating the acetylation of RelA. By "transcriptional activity of NF-κB" is meant the ability of NF-κB to bind to a κB enhancer present in a gene that is regulated by NF-κB, and, either alone or through interaction with other transcriptional factors, modulate expression of the gene, e.g., facilitate an increase in transcription of the gene. It is also possible to use NF-κB as a negative regulator of transcription.

The activity of agents of interest can be identified, and their effects described, according to the biological phenomenon they affect. For example, agents of interest can be identified and/or characterized in terms of their effect upon the acetylation of RelA, upon the nuclear export of RelA, or upon the transcriptional activity of NF-κB.

Exemplary agents of interest thus include those that, for example, increase the relative amount of deacetylated RelA (e.g., in the cell or in the sample in a cell-free assay, as measured either qualitatively or quantitatively) increases at least about 10%, at least about 15%, at least about 20%, at least about 25%, more preferably at least about 50%, more preferably at least about 100%, or 2-fold, more preferably at least about 5-fold, more preferably at least about 10-fold or more when compared to a suitable control (e.g., relative to a level in the absence of the agent). Additional exemplary agents of interest include those that increase acetylation of RelA at levels similar to those described above (e.g., increase acetylation of RelA at least about 10%, and so forth as detailed above.)

Exemplary agents of particular interest also include those that decrease the transcriptional activity of NF-κB (e.g., as measured either qualitatively or quantitatively by detection of a level of expression of a control gene known to be positively regulated by NF-κB) by at least about 10%, at least about 15%, at least about 20%, at least about 25%, more preferably at least about 50%, more preferably at least about 100%, or 2-fold, more preferably at least about 5-fold, more preferably at least about 10-fold or more when compared to a suitable control (e.g., relative to a level in the absence of the agent and under conditions that normally result in expression of the control gene). Additional exemplary agents of interest include those that increase NF-κB transcriptional activity at levels similar to those described above (e.g., increase NF-κB transcriptional activity at least about 10%, and so forth as detailed above).

Exemplary agents of particular interest further include those that increase in export of RelA from the nucleus at least about 10%, at least about 15%, at least about 20%, at least about 25%, more preferably at least about 50%, more preferably at least about 100%, or 2-fold, more preferably at least about 5-fold, more preferably at least about 10-fold or more when compared to a suitable control (e.g., relative to a level in the absence of the agent).

Generally a plurality of assay mixtures is run in parallel with different agent concentrations to obtain a differential response to the various concentrations. Typically, one of these concentrations serves as a negative control, i.e., at zero concentration or below the level of detection.

Agents that exhibit the desired activity and to the desired extent may be selected for further study, and assessed for bioavailability, cytotoxicity, biocompatibility, etc. For example, a candidate agent is assessed for any cytotoxic activity it may exhibit toward a eukaryotic cell, using well-known assays, such as trypan blue dye exclusion, an MTT (3-(4,5-dimethylthiazol-2-yl)-2,5-diphenyl-2 H-tetrazolium bromide) assay, and the like. Agents that do not exhibit cytotoxic activity toward eukaryotic cells are considered candidate agents for use in therapeutic methods for treating immunological diseases.

Assays

A wide variety of assays can be used to screen candidate agents, including labeled in vitro binding assays, e.g., competitive binding assays, electrophoretic mobility shift assays, immunoassays for protein binding, and the like. Isolated, naturally-occurring or recombinant HDAC3, RelA and NF-κB proteins, and/or synthetically produced peptides or fragments of HDAC3, RelA, and NF-κB can be used in various screening assays to identify ligands or substrates that bind to, modulate (e.g., increase or inhibit), or mimic the action of the native proteins. The purified proteins may also be used for determination of three-dimensional crystal structure, which can be used for modeling intermolecular interactions, transcriptional regulation, etc.

The screening assay can be a binding assay (e.g., to detect binding of NF-κB to a κB sequence of a nucleic acid molecule or to detect formation of RelA and p50 in the NF-κB complex); wherein one or more of the molecules may be joined to a label, and the label directly or indirectly provides a detectable signal. Various labels include radioisotopes, fluorescers, chemiluminescers, enzymes, specific binding molecules, particles, e.g., magnetic particles, and the like. Specific binding molecules include pairs, such as biotin and streptavidin, digoxin and antidigoxin. For the specific binding members, the complementary member would normally be labeled with a molecule that provides for detection, in accordance with known procedures. In general, the particular type of screening assay employed will preferably be amenable to parallel, simultaneous screening of a large number of candidate agents.

A variety of other reagents may be included in the screening assays described herein. Where the assay is a binding assay, these include reagents like salts, neutral proteins, e.g. albumin, detergents, etc. that are used to facilitate optimal protein-protein binding, protein-DNA binding, and/or reduce non-specific or background interactions. Reagents that improve the efficiency of the assay, such as protease inhibitors, nuclease inhibitors, anti-microbial agents, etc. may be used. The mixture of components is added in any order that provides for the requisite binding. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

In general, having described the discovery herein that deacetylation of RelA leads to I-κBα binding and decreased NF-κB transcriptional activity, one of ordinary skill in the art can readily design and conduct assays to identify agents that have such activity using methods and compositions readily available in the art. The particular type of assays can be readily selected and designed according to a variety of factors such as the activity to be measured will be selected according to a variety of factors such as the number and type of agents to be screened (e.g., design of the assay for high-throughput screening), and other variables. Furthermore, and as described above, the effect of candidate agents can be detected in a variety of ways, for example, through detection of RelA acetylation/deacetylation, detection of association of RelA-IκBα complexes, detection of a level of RelA in the nucleus, detection of NF-κB binding to DNA, detection of NF-κB transcriptional activity (e.g., using a reporter gene) the activity the screening assay, and the like). The assays described below are thus exemplary, and are not meant to be limiting in any way.

Cell-free assays

Cell-free assay methods generally comprise: a) contacting a test agent with a sample having an acetylated RelA subunit (e.g., isolated or within an NF-κB complex of p50 and RelA); and b) assaying for a phenomenon associated with deacetylation of the RelA in the presence of the agent. Such phenomena include, but are not necessarily limited to, direct detection of deacetylated and/or acetylated RelA, detection of NF-κB complexes having p50 and RelA, detection of NF-κB binding to DNA, and, where the cell-free assay is an in vitro transcription assay, detection of NFκB-mediated transcription of a reporter gene having κB enhancer sequences. An increase or a decrease in the measured activity in comparison to the activity in a suitable control (e.g., a sample comprising an HDAC3 molecule in the absence of the agent being tested, or a sample lacking the agent) is an indication that the agent modulates NF-κB activity.

Cell-free assays can be conducted in a variety of ways. For example, where the assays is based on detection of deacetylation of RelA, the assays can comprise combining a candidate agent with detectably labeled, acetylated RelA, where the detectable label is released from RelA upon deacetylation. In one embodiment, such detectably labeled, acetylated RelA is prepared by use of Na-[$^3$H]-acetate. Activity of the candidate agent in deacetylation of RelA can be assessed by detecting released detectable label, or by assessing a decrease in detectable label associated with RelA. The results obtained with the candidate agent are compared to an appropriate control, e.g., a mock-treated sample in the absence of candidate agent, or a sample having an agent of known activity in deacetylating RelA, e.g., HDAC3.

In another embodiment, the candidate agent is screened for RelA deacetylation activity by competitive binding of the candidate agent with RelA in the presence of HDAC3. Methods for carrying out such competitive binding assays are well known in the art.

In another embodiment, the candidate agent is screened for its effect upon the level (either qualitative or quantitative) of RelA binding to IκBα (e.g., the formation of RelA-IκBα complexes. An increase in RelA-IκBα complexes indicates that the agent has activity in deacetylation of RelA, and thus has activity in decreasing NF-κB transcriptional activity. A decrease in in RelA-IκBα complexes indicates that the agent has activity in acetylation of RelA (making it unavailable for binding to IκBα), and thus has activity in increasing NF-κB transcriptional activity.

In another embodiment, the candidate agent is combined with detectably labeled NF-κB, and the ability of NF-κB to bind a nucleic acid molecule having at least one κB sequence is assessed. A decrease in NF-κB binding to κB sequences indicates that the NF-κB complex has been disrupted by the candidate agent, which can be a result of deacetylation of RelA by the candidate agent. The assay is generally conducted in the presence of suitable controls, e.g., in the presence of HDAC3, in the absence of candidate agent, etc.

Cell-based Assays

Cell-based assays generally involve contacting a cell that produces NF-κB with a test agent, and determining the effect of the candidate agent upon NF-κB activity via deacetylation of the RelA subunit. A cell may produce the NF-κB or RelA endogenously, or be modified to expression a recombinant NF-κB or RelA.

Cells suitable for use in cell-based assays include any eukaryotic cell, generally any higher eukaryotic cell, usually a mammalian cell, that expresses or can be modified to express, a functional NF-κB complex. In one embodiment, the cells are easily manipulated, easily cultured mammalian cell lines, preferably human cell lines, such as, but nor necessarily limited to 293 cells, HeLa cells, Jurkat T cells, and the like. An assay using cell-based systems can be optionally conducted in the presence of an NF-κB inducer, such as TNF-α.

In one embodiment, activity of candidate agents in affecting NF-κB activity by deacetylation of RelA is assessed by detectably labeling RelA with a detectable label that is released upon deacetylation, e.g., Na-[$^3$H]-acetate. In general, the cells are grown in a culture medium in the presence of labeled acetate. After washing away excess detectable label, the cell is then contacted with the test agent. After a period of time, such as 30 minutes, 1 hour, 2 hours, 4 hours, or 12 hours, deacetylation of RelA is assessed by either release of the detectable label or by assessing the amount of detectable label associated with RelA, e.g., by preparing an extract of the cells, and measuring the amount of radioactivity in a deacetylated RelA subunit, e.g., using thin-layer chromatography or some other technique known to one of skill in the art. Isolation of RelA for analysis in any assay can be accomplished by, for example, immunoprecipitation using an anti-RelA antibody, or by modifying RelA to include an epitope tag (e.g., T7, FLAG epitope, and the like) and using an anti-epitope tag antibody to isolate RelA. The assays are conducted in conjunction with one or more appropriate controls, e.g., assays in the absence of candidate agent or in the presence of a positive control, e.g., HDAC3. Where HDAC3 is to be used as a control, it is preferred that the host cell not produce a substantial amount of HDAC3, or is treated to block HDAC3 activity (e.g., by treatment with trichostatin A (TSA)).

In another embodiment, activity of a candidate agent in deacetylation of RelA is assessed by examining nuclear export of deacetylated RelA. For example, RelA is detectably labeled in the host cell, and the cell contacted with the candidate agent for a sufficient period of time. The relative location of the detectable label in the cell is then assessed. Where the detectable label is fluorescent, analysis can be accomplished by fluorescence microscopy to assess the relative levels of detectable label in the cytoplasm or the nucleus of the whole cell. Alternatively, or in addition, analysis can be accomplished by comparing the relative amounts of detectable label in samples of host cell cytoplasm relative to host cell nuclear extracts. Movement of the detectable label into the cytoplasm indicates that the candidate agent has activity in deacetylation of RelA, and thus activity in inhibiting NF-κB activation of transcription.

In another embodiment, the cell is treated with candidate agent, and the ability of nuclear extracts having NF-κB to bind a nucleic acid molecule having a κB sequence is assessed. A decrease in NF-κB binding to κB sequences indicates that the NF-κB complex has been disrupted by the candidate agent, which can be a result of deacetylation of RelA by the candidate agent. The assay is generally conducted in the presence of suitable controls, e.g., in the presence of HDAC3, in the absence of candidate agent, etc.

In another embodiment, the cells are modified to express a NF-κB-regulated reporter construct, and the effect of candidate agent upon reporter construct expression assessed by detection of a reporter construct gene product (e.g., reporter gene transcript or reporter polypeptide). The assay is generally conducted with appropriate controls, e.g., using host cells further modified to express HDAC3. Exemplary reporter constructs include, but are not necessarily limited to, green fluorescent protein (GFP), luciferase, β-galactosidase, CAT, and the like. Acetylation levels of RelA may be detected by using an anti-acetylated lysine antibody. The effect of a candidate agent on the acetylation level of RelA can by detected by using this antibody.

A variety of other reagents may be included in the screening assays described above. These include reagents like salts, neutral proteins, e.g., albumin, detergents, etc., that are used to facilitate optimal protein-protein binding and/or reduce non-specific or background interactions.

Reagents that improve the efficiency of the assay, such as protease inhibitors, nuclease inhibitors, anti-microbial agents, etc. may be used.

The above screening methods may be designed a number of different ways, where a variety of assay configurations and protocols may be employed, as are known in the art. For example, in cell-free assays one of the components (e.g., RelA) may be bound to a solid or semi-solid (e.g., gel) support (e.g., through cross-linking or through modification of RelA to include a tether to bind the polypeptide to a support), and the remaining components contacted with the support bound component.

The components of the method may be combined at substantially the same time or at different times. Incubations are performed at any suitable temperature, typically between 4° C. and 40° C. Incubation periods are selected for optimum activity, but may also be optimized to facilitate rapid high-throughput screening. Typically between 0.1 and 1 hours will be sufficient. Following the contact and incubation steps, the subject methods will generally, though not necessarily, further include a washing step to remove unbound components, where such a washing step is generally employed when required to remove label that would give rise to a background signal during detection, such as radioactive or fluorescently labeled non-specifically bound components.

Incubation times, e.g., for incorporation of a detectable label, to allow interaction of the candidate agent, and the like, will be selected so as to be a time sufficient to allow a desired event take place. In general, such incubation times can be varied and samples analyzed at various time points where desired. In addition, guidance for appropriate incubation times can be provided by control samples, e.g., samples having HDAC3.

Automated Screening Methods

The methods of the present invention may be automated to provide convenient, real time, high volume methods of screening compounds for activity in modulation of RelA deacetylation, and thus modulation of NF-κB activity. Automated methods are designed to detect changes in RelA acetylation and/or NF-κB activity over time (i.e., comparing the same apparatus before and after exposure to a test sample), or by comparison to a control apparatus, which is not exposed to the test sample, or by comparison to pre-established indicia. Both qualitative assessments (positive/negative) and quantitative assessments (comparative degree of translocation) may be provided by the present automated methods.

An embodiment of the present invention includes an apparatus for determining RelA nuclear export in a test sample of cells. This apparatus comprises means, such as a fluorescence measurement tool, for measuring change in fluorescence associated with RelA export in response to a particular candidate agent. The automated screening methods are possible because when RelA is deacetylated it will bind to IκBα, and the nuclear localization signal (NLS) of RelA will again be masked by the IκBα. By using an antibody against the NLS of RelA, it is possible to detect whether RelA is bound to IκBα or not. It is also possible to use an antibody to detect the presence of acetylated RelA.

Measurement points may be over time, or among test and control samples. A computer program product controls operation of the measuring means and performs numerical operations relating to the above-described steps. The preferred computer program product comprises a computer readable storage medium having computer-readable program code means embodied in the medium. Hardware suitable for use in such automated apparatus will be apparent to those of skill in the art, and may include computer controllers, automated sample handlers, fluorescence measurement tools, printers and optical displays. The measurement tool may contain one or more photodetectors for measuring the fluorescence signals from samples where fluorescently detectable molecules are utilized. The measurement tool may also contain a computer-controlled stepper motor so that each control and/or test sample can be arranged as an array of samples and automatically and repeatedly positioned opposite a photodetector during the step of measuring fluorescence intensity.

The measurement tool is preferably operatively coupled to a general purpose or application specific computer controller. The controller preferably comprises a computer program produce for controlling operation of the measurement tool and performing numerical operations relating to the above-described steps. The controller may accept set-up and other related data via a file, disk input or data bus. A display and printer may also be provided to visually display the operations performed by the controller. It will be understood by those having skill in the art that the functions performed by the controller may be realized in whole or in part as software modules running on a general purpose computer system. Alternatively, a dedicated stand-alone system with application specific integrated circuits for performing the above described functions and operations may be provided.

Identified Candidate Agents in Pharmaceutical Compositions and Methods of Treatment Candidate agents identified as modulating NF-κB activity (e.g., increasing NFκB activity or, generally more preferably, inhibiting NF-κB activity) can be formulated in a pharmaceutical composition and can be used in methods of treatment of a subject, e.g., human or other animal, such as mammals, livestock and other domesticated animals (e.g., cattle, swine, hogs, sheep, goats, cats, dogs, birds), and the like.

The agents may be prepared as formulations at a pharmacologically effective dose in pharmaceutically acceptable media, for example normal saline, PBS, etc. The additives may include bactericidal agents, stabilizers, buffers, or the like. The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Various methods for administration may be employed, and will vary according to a variety of factors, such as the agent to be delivered, the formulation used, route of delivery, the condition to be treated, and the like. The formulation may be given orally, or may be injected intravascularly, subcutaneously, peritoneally, etc. Methods of administration by inhalation are well-known in the art. The dosage of the therapeutic formulation will vary widely, depending upon the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc. to maintain an effective dosage level. In many cases, oral administration will require a higher dose than if administered intravenously.

The agents may be administered as a combination therapy with other suitable pharmacologically active agents. The additional drugs may be administered separately or in conjunction with the peptide compositions, and may be included in the same formulation. For example, where the condition to be treated is an inflammatory condition, the agent can be administered with one or more compatible anti-inflammatory agents.

In general, the agent is present in the therapeutic formulation, or administered, in an effective amount to provide for the desired effect in the subject treated. The terms "effective amount" and/or "therapeutic amount" means a dosage sufficient to provide treatment for the disease state being treated. This will vary depending on the patient, the disease and the treatment being effected. In the case of a bacterial infection, an "effective amount" is that amount necessary to substantially improve the likelihood of treating the infection, in particular that amount which improves the likelihood of successfully preventing infection or eliminating infection when it has occurred.

The terms "treatment," "treating" and the like, are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease.

Conditions Amenable to Treatment Using Agents that Modulate NF-κB Activity

In general, agents that modulate NF-κB activity through modulating the acetylation of RelA can be used to treat any condition that is associated with NF-κB transcriptional activity, particularly increased NF-κB activity. For example, inhibition of NF-κB activation provides a therapeutic mechanism for treatment of conditions, including symptoms of such conditions that are caused by or associated with induction of NF-κB activity. In particular, the agents identified herein that have activity in increasing the deacetylation of RelA, and thus act to inhibit NF-κB activity within the nucleus are of particular use for treatment of conditions associated with constitutive localization and action of NF-κB in the nucleus. As discussed above, most conventional therapeutics act upon NF-κB in the extranuclear cytoplasm. The present invention thus represents an advance in providing additional therapeutic targets that act upon activated NF-κB (e.g., NF-κB that has been "unmasked" and transported into the nucleus).

Of particular interest is the treatment of those conditions that are the result of gene expression or gene expression pathways positively regulated by NF-κB. Some examples of genes and pathways positively regulated by NF-κB include the response to and induction of IL-2, the induction of TAP1 and MHC molecules by NF-κB, and many aspects of the inflammatory response, e.g. induction of IL-1 ($\alpha$ and $\beta$), TNF-$\alpha$ and leukocyte adhesion molecules (E-selectin, VCAM-1 and ICAM-1). Moreover, NF-κB is involved in many aspects of cell growth, differentiation and proliferation via the induction of certain growth and transcription factors (e.g., c-myc, ras and p53). NF-κB itself is induced by stimuli such as pro-inflammatory cytokines and bacterial toxins (e.g., LPS, exotoxin B) and a number of viruses/viral products (e.g., HIV-1, HTLV-1, HBV, EBV, Herpes simplex) as well as pro-apoptotic and necrotic stimuli (oxygen free radicals, UV light, gamma-irradiation).

Specifically, the deacetylation of RelA may be used in the treatment of conditions characterized by acute or chronic inflammation. Thus, conditions amenable to treatment using agents that promote deacetylation of RelA include, but are not necessarily limited to, inflammatory illnesses resulting from an activation of T cells, macrophages or B cells, toxic shock, illness after infection by a virus containing the κB motif, UV-damage (sunburn), radiation damage, burns, and transplant rejection.

Treatment of inflammatory conditions using agents that inhibit NF-κB activity is of particular interest. Exemplary inflammatory conditions associated with aberrant NF-κB activity include, but are not necessarily limited to, asthma, rheumatoid arthritis, and atherosclerosis. For a review of inflammatory conditions that are associated with increased NF-κB activity and a discussion of the therapeutic application of regulation of the NF-κB pathway to inflammation, see, e.g., Yamamoto et al., *J. Clin. Invest.* 107(2):135–142 (January 2001); Bours et al., *Toxicology* 153(1–3):27–38 (Novemeber 2000); Grossman et al., *Intl. J. Biochem. Cell Biol.* 31(10):1209–1219 (1999). It should be noted that NF-κB activity has also been associated with Alzheimer's disease.

HIV-1 infection can be treated with agents that promote deacetylation of RelA. Repression of the activation of latent HIV, by administration of an agent that promotes deacetylation of RelA is of particular interest. Treatment of latently HIV-infected T-cells with phorbol ester (12-O-tetradecanoylphorbol 13-acetate; TPA) and with phytohemaglutinin (PHA) results in the onset of virus production. See, Harada, S. et al., *Virology* 154:249–258 (1986); and Zagury, D. J. et al., *Science* 232:755–759 (1986). These same treatments induce NF-κB activity in the human T-lymphoma cell line. See, Sen, R. and Baltimore, D., *Cell* 47:921–928 (1986). The identification of two NF-κB binding sites located upstream of the transcriptional start site in the HIV enhancer led to the discovery that NF-κB is the key physiological transactivator responsible for initial expression of dormant HIV-DNA following stimulation of Tlymphocytes. See, U.S. Pat. No. 6,150,090 and Nabel et al., *Nature* 326:711–713 (1987).

The treatment of autoimmune disease, where NF-κB is overexpressed, is also of interest. Heightened immune reactions mediated by NF-κB could be ameliorated by agents that promote RelA deacetylation.

Modulation of NF-κB also has implications for treatment of microbial infections (e.g., bacteria, yeast, parasites, and the like) in addition to those by viruses. For example, modulation of NF-κB activity can modulate the availability of host cell receptors that mediate binding or other process important to pathogenesis. For example, pathogenic Neisseria bacteria increase expression of their CEACAM1 (CD66a) receptor on primary endothelial cells by activating NF-κB (Muenzer et al., *J. Biol. Chem.* (Apr. 16, 2001) epub). Thus, inhibiting NF-κB activity can be used to decrease the availability of such receptors, thus inhibiting and treating infection.

Constitutive NF-κB activity has been found in the nucleus of several types of cancer cells. For example, NF-κB has been shown to regulate cyclooxygenase-2 expression and cell proliferation in human gastric cancer cells (see, Lim et al., *Lab. Invest.* 81(3):349–360 (March 2001)). NF-κB also mediates an antiapoptotic effect in renal cell carcinoma. NF-κB is also implicated in HTLV-I-induced T cell leukemia (see, Nabel, G. . and Verma, I. M. *Genes Dev.* 7:2063 (1993). In another example, inhibition of NF-κB enhances apoptosis in human lung adenocarcinoma cells. For a review of NF-κB in the control of oncogenesis and cancer therapy resistance see, e.g., Baldwin, *J. Clin. Invest.* 107(3):241–246 (February 2001).

In addition, inhibition of NF-κB has been shown to enhance the sensitivity of cancer cell lines to antineoplastic- or radiation-induced apoptosis, and suppression of NF-κB results in attenuation of cancer cachexia in a mouse tumor model (see, e.g., Schwartz et al., *Surg. Oncol.* 8(3):143–153 (1999)). For reviews of the role of NF-κB pathway and the role of its regulation in cancer therapy see, e.g., Yamamoto et al., *J. Clin. Invest.* 107(2):135–142 (January 2001); Bours et al., *Toxicology* 153(1–3):27–38 (November 2000); Bours et al., *Biochem. Pharmacol.* 60(8):1085–1089 (October 2000); Mayo et al., *Biochim. Biophys. Acta* 1470(2):M55–62 (March 2000); Schwartz et al., *Surg. Oncol.* 8(3):143–153 (1999). Therefore, agents identified as modulators of NF-κB activity (e.g., inhibitors of NF-κB activity) according to the methods of the invention can also be used in the treatment of cancer in a subject.

In other embodiments, the invention provides for agents that increase NF-κB transcriptional activity by increasing acetylation of RelA. Such agents that increase NF-κB activity are of interest for treatment of conditions associated with immunodeficiencies reflecting diminished NF-κB action. Increasing NF-κB in such conditions can boost the immune system.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

TSA Enhances TNF-α Induction of NF-κB DNA Binding Activity and Function by Prolonging Intranuclear Expression of RelA

Figure 1B:
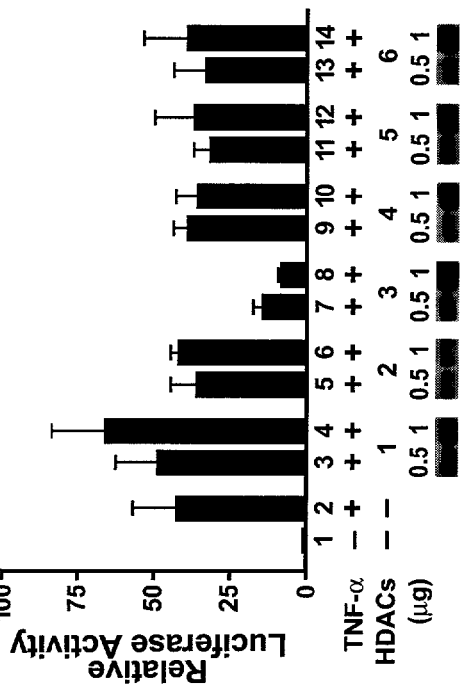
FIG. 1B shows nuclear extracts prepared from HeLa cells treated with different amounts of TSA and/or TNF-α. The results show enhanced levels of DNA binding activity with the pre-treated TSA cultures in the presence of TNF-α.
Figure 1C:
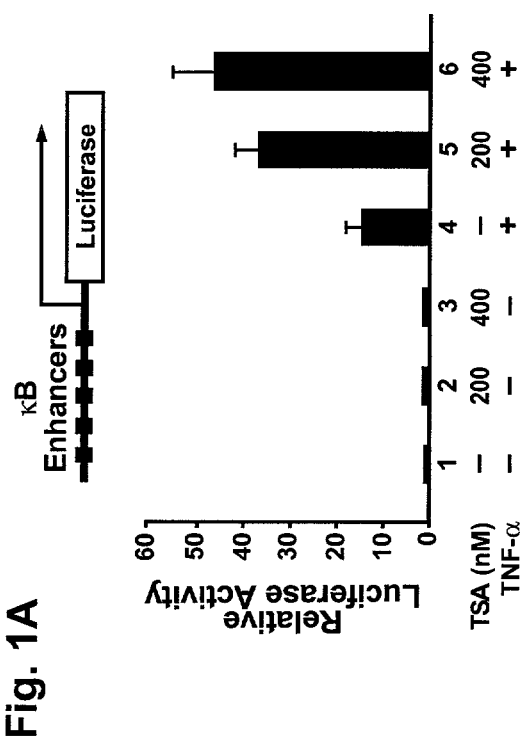
FIG. 1C is a photograph of a gel showing the TSA treatment promotes higher intranuclear levels of RelA expression.
Figure 1D:
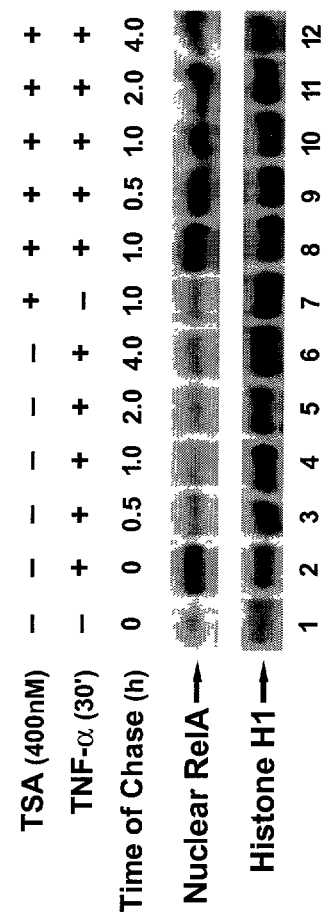
FIG. 1D is a bar graph showing that HDAC3 selectively inhibits TNF-α induced κB-luciferase activity.
Figure 1E:
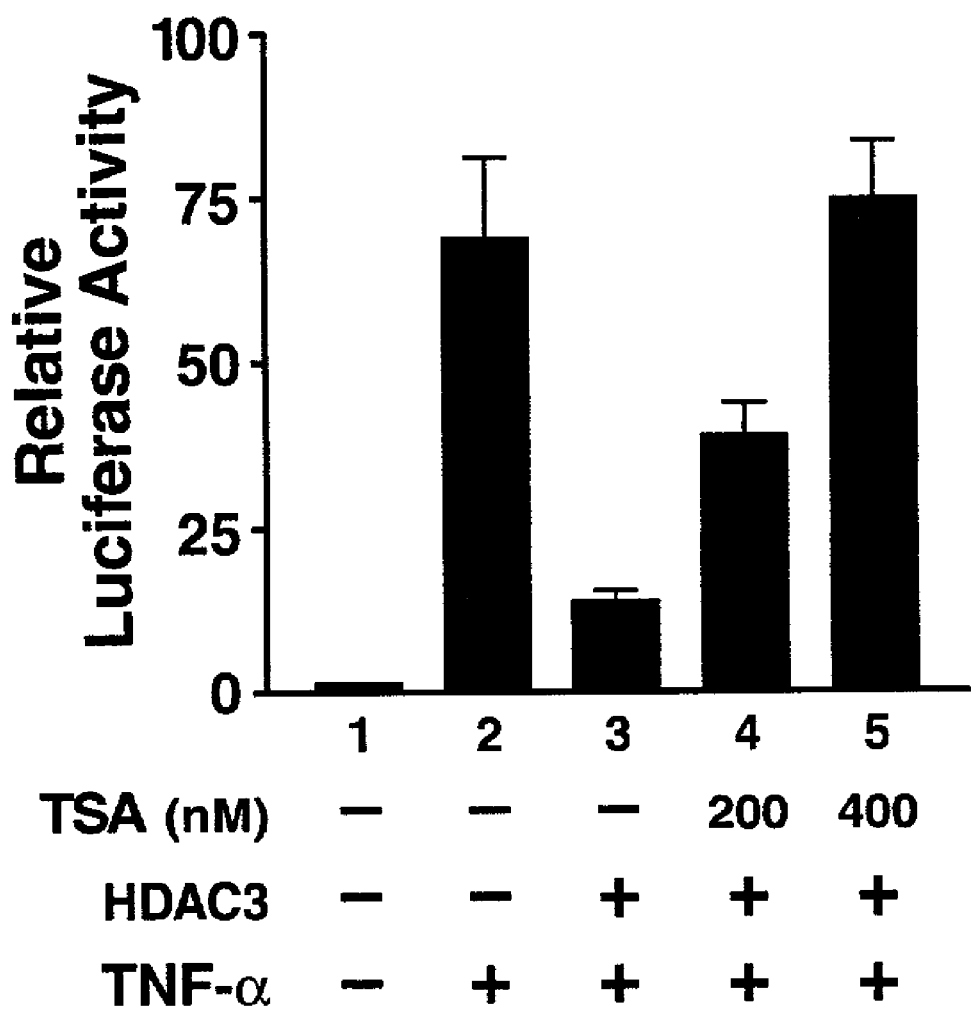
FIG. 1E is a bar graph showing that TSA treatment blocks the inhibitory effects of HDAC3 on TNF-αactivation of κB-luciferase.

It is well known that TSA broadly inhibits the action of the HDACs. Because the HDACs not only deacetylate core histones leading to repressive changes in chromatin structure but also deacetylate various host transcription factors producing changes in their transcriptional activity (see, Kouzarides, M. T., *EMBO J.* 19:1176–1179 (2000)), potential inhibitory effects were assessed for several of the known HDACs on NF-κB action (FIG. 1D). For these analyses, 293T cells were co-transfected with expression vector DNA encoding HDAC1, 2, 3, 4, 5 or 6 and a κB luciferase reporter followed by stimulation of the cell cultures with TNF-α for 5 hours (FIG. 1D). Although each of the HDACs was comparably expressed, only HDAC3 inhibited the increase in κB-luciferase activity occurring in response to TNF-α induction (FIG. 1D, lanes 7 and 8). Similarly, activation of the κB-luciferase reporter by co-expression of RelA was selectively inhibited by HDAC3 (data not shown). These inhibitory effects of HDAC3 were abrogated in the presence of TSA suggesting that the deacetylase function of HDAC3 was required for these biological effects (FIG. 1E).

To show that trichostatin A (TSA) enhances TNF-α mediated activation of κB-luciferase gene expression, 293T cells were transfected using FuGENE 6 (Roche) with 0.1 μg of κB-luciferase reporter plasmid DNA (Stratagene). After 24 hours, the cultures were treated with the indicated concentrations of TSA for 1 hour prior to stimulation with TNF-α (10 ng/ml). Cell lysates were prepared 5 hours later and luciferase activity measured.

For the luciferase reporter assays, 293T cells were seeded into either 24 well ($1\times10^5$ cells per well) or 6 well ($4\times10^5$ cells per well) plates and cultured for 10–12 hours in DMEM-10% FCS before transfection. Plasmid DNA was transfected using FuGENE 6 (Roche). At 16–24 hours after transfection, cells were lysed with 5× passive lysis buffer (Promega). In each experiment, cells were also co-transfected with EF1α-Renilla luciferase reporter plasmids to permit normalization for differences in transfection efficiency occurring in the individual cultures. Firefly and Renilla luciferase activity were assayed using the dual luciferase assay system according to the manufacturer's instructions (Promega). The results are shown in FIG. 1A. Error bars indicate standard deviation derived from three independent transfections.

To show that TSA enhances TNF-α induction of nuclear NF-κB binding activity, nuclear extracts were prepared from HeLa cells pretreated for 4–5 hours with media or the indicated concentrations of TSA. This was followed by stimulation of the cultures with media alone or with TNF-α (10 ng/ml) for 10 minutes. NF-κB DNA binding activity was assessed in electrophoretic mobility shift assays (EMSA) using a [$^{32}$P]-radiolabeled consensus κB enhancer oligonucleotide (5'-agt tga ggg gac ttt ccc agg c-3'SEQ ID NO:3) (FIG. 1B, upper panel). The results of supershifting of this complex with anti-RelA (SC-109, Santa Cruz) and anti-p50 (SC-1190, Santa Cruz) antibodies are shown in lanes 7 and 8. Comparability of the various nuclear extracts was assessed by EMSA using a $^{32}$P-radiolabeled Sp1 probe (Promega) (lower panel).

Next was to determine whether RelA expression is sustained in the nuclei of TNF-α stimulated cells in the presence of TSA. First, HeLa cells were incubated in the presence (FIG. 1C, lanes 7–12) or absence (lanes 1–6) of TSA (400 nM) for one hour prior to stimulation with TNF-α (20 ng/ml) for 30 min. The cells were then washed and cultured for the indicated time periods in media alone (lanes 1–6) or medium containing TSA (400 nM) (lanes 7–12). Nuclear extracts were prepared from each culture and immunoblotted with anti-RelA antibodies (SC-109, Santa Cruz) and visualized using an enhanced chemiluminesence (ECL) reagent (Amersham). The results show that RelA expression is sustained in the nuclei of TNF-α stimulated cells in the presence of TSA.

Finally, it was investigated which of the HDACs best inhibited TNF-α activation of κB-luciferase activity. Expression plasmids encoding each of the indicated FLAG- HDACs were co-transfected at two concentrations (0.5 or 1.0 µg of DNA) into 293T cells with κB-luciferase reporter plasmid DNA (0.1 µg). 16 hours later, TNF-α (10 ng/ml) was added to the indicated cultures and luciferase activity was measured 5 hrs later. Expression levels of each HDAC determined by anti-FLAG immunoblotting of the cell lysates are shown in the insets.

For the immunoprecipitation and immunoblotting analyses, transfected COS-7 cells or 293T cells cultured in 6 well plates were lysed in 300 µl of lysis buffer (50 mM HEPES, pH 7.4, 250 nM NaCl, 1% NP-40, 1 mM EDTA). Lysates from 2 or 3 wells were immunoprecipitated for 2 hours at 4° C. using 20 µl of a slurry containing 50% anti-T7-conjugated agarose beads (Novagen). These immunoprecipitates were washed three times in lysis buffer. Immunoprecipitated proteins were separated by SDSPAGE (10%), transferred to nitrocellulose transfer membranes and immunoblotted with various antibodies followed by visualization of the immunoreactive proteins by ECL (Amersham). The bar graph (FIG. 1D) shows that histone deacetylase 3 (HDAC3), but not HDAC1, 2, 4, 5 or 6, inhibits TNF-α activation of κB -luciferase activity.

The sum of the experiments show that Trichostatin A (TSA), a specific inhibitor of the multiple histone deacetylases (HDACs), enhanced TNF-α induced, but not basal, expression of a κB-luciferase reporter gene expression (FIG. 1A). TSA also enhanced nuclear NF-κB DNA binding following TNF-α stimulation but did not stimulate NF-κB binding in the absence of this agonist (FIG. 1B). TSA did not alter the binding of the constitutively expressed Sp1 transcription factor either in the presence or absence of TNF-α (FIG. 1B, lower panel). Supershifting with anti-RelA and anti-p50 specific antibodies confirmed the participation of both of these components of the classical NF-κB transcription factor in these induced nucleoprotein complexes (FIG. 1B, lanes 7, 8). Potential effects of TSA on the intranuclear levels of RelA were next evaluated (FIG. 1C). Nuclear extracts were prepared from HeLa cells stimulated with TNF-α for 30 minutes, washed, and then cultured in medium for 0–4 hours. Immunoblotting of these nuclear extracts with anti-RelA antibodies revealed sustained nuclear RelA expression in the presence of TSA. Together, these results indicate that TSA enhances TNF-α induction of NF-κB DNA binding activity and function likely by prolonging intranuclear expression of RelA.

Example 2

RelA is Acetylated in a Signal-coupled Manner and Mediated by p300 and CBP

In view of these inhibitory effects of HDAC3 and suppression of the HDAC3 effect by TSA, it was next investigated whether the RelA subunit of NF-κB is acetylated in vivo. COS7 cells were co-transfected with expression vectors encoding T7-RelA and HDAC1 or HDAC3. 24 hours later, the cultures were radiolabeled for 1 hour with Na-[$^3$H]-acetate (1 mCi/ml) in the presence of cycloheximide (25 µg/ml) to block potential transmigration of the radiolabel during protein synthesis. One sample of the cells was treated with TSA (400 nM) to block HDAC activity. Cell lysates were prepared and immunoprecipitated (IP) with anti-T7 antibodies (Novagen) to evaluate potential in vivo acetylation of RelA. The total amount of T7-RelA in the individual samples determined by sequential immunoprecipitation and immunoblotting (IB) with anti-RelA antibodies is shown in the lower panel of FIG. 2A.

Figure 2A:
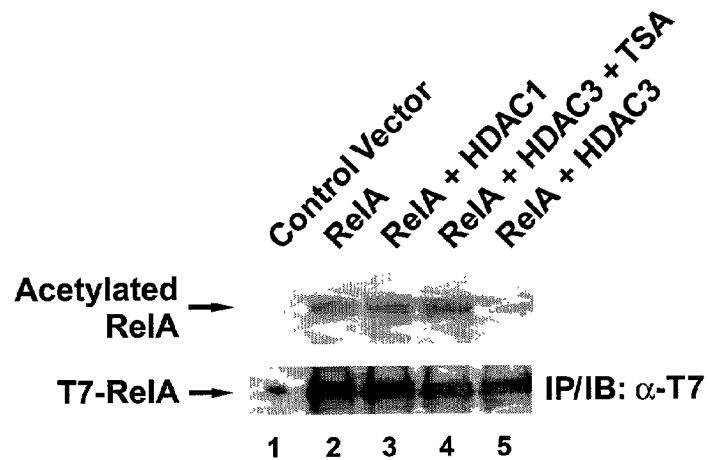
FIGS. 2A–D show the RelA subunit is acetylated in vivo and that p300 and CBP can mediate such acetylation.

These studies reveal that RelA is acetylated in vivo (FIG. 2A, lane 2, upper panel) and further that this acetylation was not detected in the presence HDAC3 expression (FIG. 2A, lane 5). See, Gu, W. and Roeder, R. G., *Cell* 90:595–606 (1997).

For in vivo assay of acetylation, COS7 cells seeded in 100 mm dishes were transfected with T7-RelA (5 µg) in combination with HDAC1 (10 µg) or control plasmid DNA (10 µg) using FuGENE 6 (Roche). Thirty hours after transfection, the cells were pretreated with cycloheximide (CHX) (25 µg/ml) for 1 hour and then transferred to the same DMEM medium containing 1 mCi/ml [$^3$H]-sodium acetate (Amersham), 25 µg/ml CHX for 1 hour at 37° C. prior to lysis. Cell lysates were immunoprecipitated with anti-T7 antibodies conjugated to agarose (Novagen). See, Beg, A. A. et al., *Mol. Cell. Biol.* 13:3301–3310 (1993).

Conversely, the expression of HDAC1 (FIG. 2A, lane 3) did not affect the detection of acetylated RelA. The addition of TSA to the HDAC3 expressing cultures was associated with detection of RelA acetylation (FIG. 2A, lane 4).

While these results indicated that overexpressed RelA is acetylated in vivo, it remained unclear whether the endogenous RelA proteins were similarly modified and whether such acetylation occurred in a signal-coupled manner. HeLa cells were stimulated with medium or TNF-α (20 ng/ml) for 30 minutes and radiolabeled for 1 hour with Na-[$^3$H]-acetate (1 mCi/ml) in the presence of cycloheximide (25 µg/ml). Whole cell lysates were prepared and immunoprecipitated (27) with anti-RelA conjugated agarose beads (SC-109AC, Santa Cruz) to evaluate the potential acetylation of RelA. Levels of RelA in the two cell lysates were determined by sequential immunoprecipitation and immunoblotting with anti-RelA antibodies (lower panel).

Figure 2B:
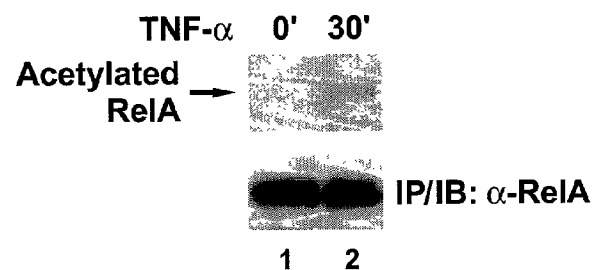

When untransfected cells were incubated in [$^3$H]-sodium acetate and stimulated with TNF-α or medium for 30 minutes followed by the immunoprecipitation of endogenous RelA, signal induced acetylation of RelA was detected (FIG. 2B).

The potential participation of the p300, CBP and P/CAF acetyltransferases in the acetylation of RelA was next investigated. 293T cells were co-transfected with T7-RelA and IκBα in the presence or absence of expression plasmids encoding the p300 acetyltransferase. Cell cultures were stimulated with TNF-α for the indicated time periods followed by immunoprecipitation of RelA with anti-T7 antibodies and immunoblotting of the immunoprecipitates with anti-acetylated lysine antibody (Cell Signaling). Levels of T7-RelA present in each of the immunoprecipitates are also shown in the lower panel.

Figure 2C:
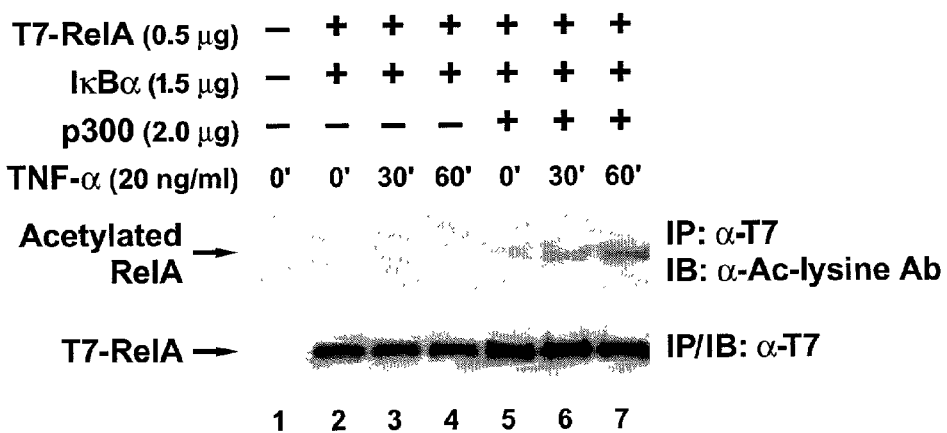
Figure 2D:
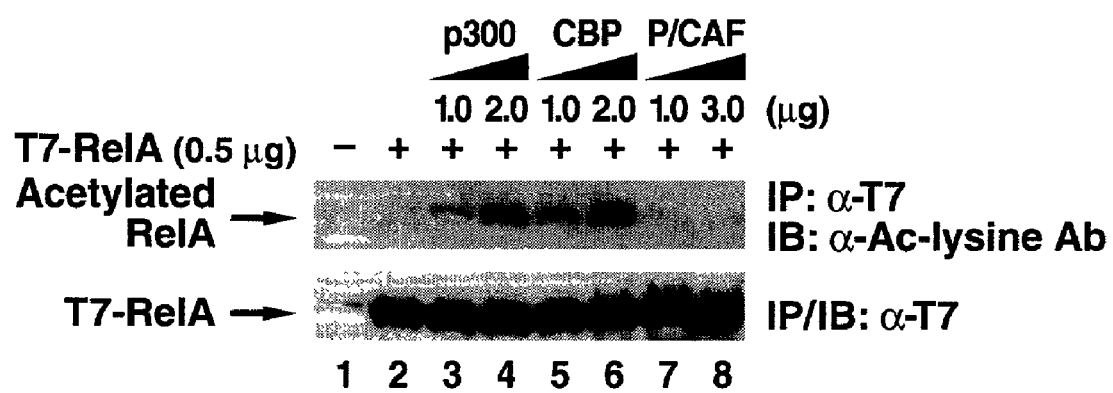

When 293T cells were co-transfected with RelA, IκBα, and p300 and stimulated with TNF-α inducible acetylation of RelA was detected by sequential immunoprecipitation of RelA and immunoblotting with an antibody specific for acetylated lysine (FIG. 2C). In the absence of co-expression of p300, TNF-α inducible acetylation of RelA was not detected. This result may stem from effective competition for endogenous p300 by other intracellular substrates as well as the use of a less-sensitive detection assay compared with the [$^3$H]-sodium acetate labeling technique utilized in FIG. 2B. These results, however, do implicate p300 as one cellular acetyltransferase that likely participates in this inducible response. Co-expression of either p300 or CBP with RelA produced dose related acetylation of T7-Rel A while P/CAF failed to mediate this response (FIG. 2D).

Together, these findings demonstrate that endogenous RelA is acetylated in a signal-coupled manner and further suggest that p300 and CBP may mediate this response.

Example 3

The N-terminal Regions of Both HDAC3 and RelA are Required for the Assembly of These Proteins in Vivo To map determinants in HDAC3 that are required for its assembly with RelA, various N- and C-terminal deletion mutants of HDAC3 were prepared and tested in co-immunoprecipitation assays (FIG. 3A-B). Deletion of either the first 120 or 45 amino acids of HDAC3 completely abolished its interaction with RelA while removal of the C-terminal 22 amino acids of HDAC3 (1–406) did not impair this assembly. Of note, the N-terminal deletion mutants of HDAC3 that failed to interact with RelA also did not inhibit RelA mediated activation of the κB-luciferase reporter compared with wild type HDAC3 (FIG. 3C). Using a mammalian two-hybrid system (Bogerd, H. and Greene, W. C., *J. Virol.* 67:2496–2502 (1993)) to study structural requirements within RelA required for its assembly with HDAC3, the N-terminal 180 amino acids comprising a portion of the Rel homology domain of RelA proved sufficient to support an interaction with HDAC3 at levels comparable to full length RelA (FIG. 3D-E). Together, these findings suggest that N-terminal regions of both HDAC3 and RelA are required for the assembly of these proteins in vivo.

Example 4

HDAC3-mediated Deacetylation of RelA Promotes its Export from the Nucleus to the Cytoplasm Studies were also performed to investigate the potential physical interaction of RelA and HDAC3 in vivo. COS7 cells were transfected with the indicated combinations of cDNAs encoding Flag-epitope tagged HDAC1 or HDAC3 and T7-RelA followed by culture for 30 hours. Cell lysates were prepared and immunoprecipitated with anti-T7 antibodies (Novagen) followed by immunoblotting with anti-Flag antibodies (D-8, Santa Cruz) (Gu, W. and Roeder, R. G., *Cell* 90:595–606 (1997)). Co-immunoprecipitation of HDAC3 but not HDAC1 with RelA is shown (compare lanes 4 with lane 3). Levels of expression of HDAC1-Flag, HDAC3-Flag and T7-RelA in these lysates are shown in the lower two panels of FIG. 3F.

Figure 3F:
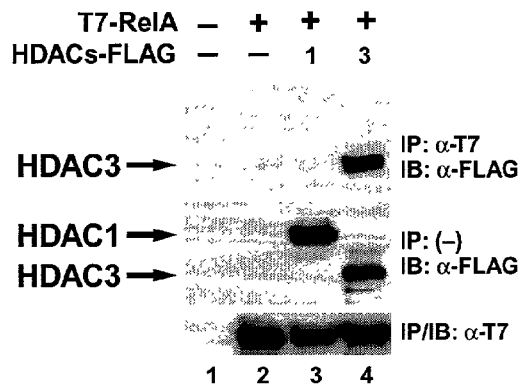
FIG. 3F is a photograph of a gel showing that HDAC3, but not HDAC1, and RelA physically assemble in vivo as evidenced by their co-immunoprecipitation.
Figure 3G:
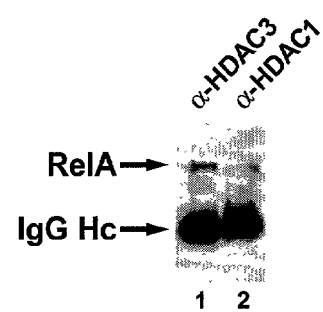
FIG. 3G is a photograph of a gel showing that endogenous HDAC3 and RelA physically associate in vivo.

In co-transfected COS-7 cells, T7-RelA and HDAC3 were effectively co-immunoprecipitated by anti-T7 antibodies (FIG. 3F). Conversely, no interaction between RelA and HDAC 1 was detected under identical conditions even though the HDAC1 and HDAC3 proteins were comparably expressed in the cellular lysates. To ensure that this interaction was not an artifact resulting from over-expression of the RelA and HDAC3 proteins, assembly of endogenous RelA and HDAC3 proteins in untransfected HeLa cells was investigated (FIG. 3F). Anti-HDAC3 antibodies effectively co-immunoprecipitated RelA from these cells while only trace amounts of RelA were detected in parallel anti-HDAC 1 immunoprecipitations (FIG. 3G).

Whole cell lysates from $10^7$ HeLa cells were immunoprecipitated with polyclonal anti-HDAC1 or anti-HDAC3 antibodies followed by immunoblotting of the immunoprecipitates with monoclonal anti-RelA antibodies (F-6, Santa Cruz). Note co-immunoprecipitation of readily detectable amounts of endogenous RelA and HDAC3 in lane 1 but only trace amounts of RelA with HDAC1 in lane 2. The prominent faster migrating band corresponds to the heavy chain of immunoglobulin (IgG Hc). Together, these findings indicate that RelA and HDAC3 assemble in vivo.

Studies were next performed to define the molecular basis for HDAC3 mediated inhibition of TNF-α activation of NF-κB. HeLa cells were transfected (50% efficiency) with control (FIG. 3H, lanes 1–4) or HDAC3 expression vector DNA and cultured for 24 hours followed by stimulation with TNF-α (10 ng/ml) for 0, 10, 30 or 90 minutes. Nuclear extracts were prepared from these cultures and EMSAs performed. Note that expression of HDAC3 diminished NF-κB (FIG. 3H, panel 1, lanes 5–8) but only modestly affected Sp1 (panel 2, lanes 5–8) DNA binding activity. Residual NF-κB DNA binding activity seen in the presence of HDAC3 likely reflects TNF-α induction occurring in the 50% of cells that were not transfected in the culture. TNF-α induced degradation of IκBα a was analyzed in the cytoplasmic extracts of these cultures by immunoblotting with anti-IκBα antibodies (C-21, Santa Cruz) (panel 3). Note the similar degree and kinetics of IκBα degradation in the HDAC3 and control DNA transfected cells. Levels of nuclear RelA were assessed by immunoblotting the nuclear extracts from the cells with anti-RelA specific antibodies (SC-109, Santa Cruz) (panel 4). The HDAC3 transfected cultures express significantly lower amounts of nuclear RelA (panel 4, compare lanes 5–8 versus lanes 1–4). The faster migrating bands reactive with the anti-RelA antibodies likely correspond to RelA degradation products and show similar changes in levels of nuclear expression.

Figure 3H:
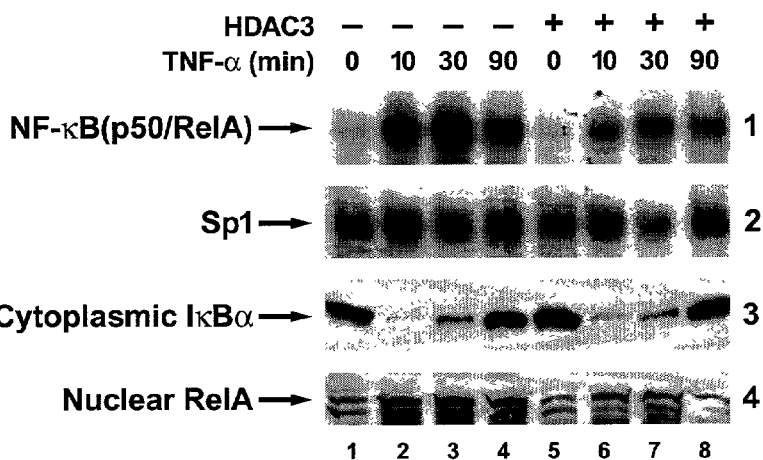
FIG. 3H is a photograph of a gel showing that HDAC3 inhibits TNF-α induced nuclear expression of RelA and NF-κB DNA-binding activity while not altering TNFα activation of IκBα degradation.

Expression of HDAC3 in HeLa cell cultures (50% transfection efficiency) produced diminished NF-κB DNA binding activity (FIG. 3H, panel 1) as well as decreased levels of nuclear RelA (panel 4). In contrast, HDAC3 expression did not alter TNF-α induced degradation of IκBα occurring in the cytoplasm (FIG. 3H, panel 3) nor markedly change the levels of Sp1 DNA binding activity present in these nuclear extracts (FIG. 3H, panel 2).

Together with the results presented in FIG. 1C, these findings suggest HDAC3 may influence the intracellular trafficking of RelA. Precedent for acetylation playing a role in the intracellular trafficking of a transcription factor is provided by recent studies of hepatocyte nuclear factor-4 and CIITA. See, Soutoglou, E. et al., *Mol. Cell.* 5:745–751 (2000) and Spilianakis, C. et al., *Mol. Cell. Biol.* 20:8489–8498 (2000). CBP mediated acetylation of HNF-4 and P/CAF mediated acetylation of CIITA are required for their nuclear retention.

Figure 3I:
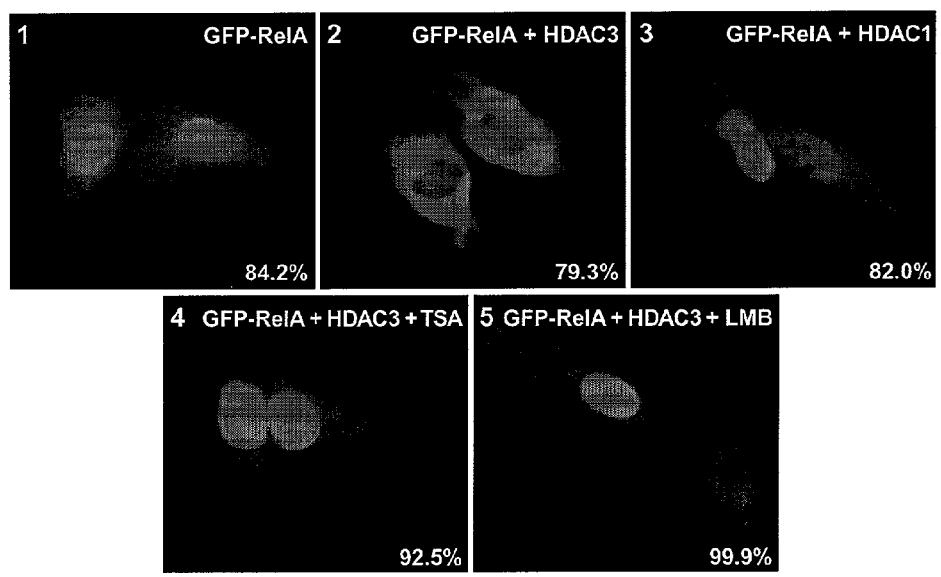
FIG. 3I is a series of five photographs of an epifluorescent study showing that HDAC3 stimulates the nuclear export of GFP-RelA via a leptomycin B (LMB) sensitive pathway. GFP-RelA fusion proteins were expressed in HeLa cells alone (Panel 1) or in the presence of HDAC3 (Panel 2), HDAC1 (Panel 3), HDAC3 and TSA (Panel 4), and HDAC3 and LMB (Panel 5).

To monitor potential effects of HDAC3 on the intracellular trafficking of RelA, green fluorescent protein-RelA fusion proteins (GFP-RelA) were prepared and expressed in HeLa cells in the presence and absence of HDAC3 (FIG. 3I). As shown in panel 1, GFP-RelA principally localized in the nucleus, however, co-expression of HDAC3 and GFP-RelA resulted in a cytoplasmic pattern of GFP-RelA epifluorescence (panel 2). HDAC3 and GFP-RelA plasmid DNA was transfected at a 6:1 ratio to ensure that all GFP-RelA expressing cells also contained HDAC3. Co-expression of HDAC1 and GFP-RelA did not alter the nuclear pattern of GFP-RelA epifluorescence (panel 3). Treatment of the GFP-RelA and HDAC3 co-transfected cell cultures with TSA (800 nM, 5 hours) to block HDAC3 enzymatic activity resulted in a nuclear pattern of expression of GFP-RelA (panel 4). Similarly, treatment of GFP-RelA and HDAC3 expressing cultures with leptomycin B (20 nM, 2 hour), which blocks CRM-1/exportin-1 dependent nuclear export (Yoshida, M. and Horinouchi, S., *Ann. N.Y. Acad. Sci.* 886:23–36 (1999)) produced a nuclear pattern of GFP-RelA epifluorescence. Numbers shown in the lower left corner of each panel represent the percentage of cells displaying the depicted phenotype derived from inspection of at least 200 transfected cells present in multiple microscopic fields.

While GFP-RelA was principally nuclear when expressed alone (FIG. 3I, panel 1), co-expression of HDAC3 produced a cytoplasmic pattern of GFP-RelA epifluorescence (FIG. 3I, panel 2). Conversely, co-expression of HDAC1 did not alter the nuclear expression of GFP-RelA (FIG. 3I, panel 3). Cytoplasmic relocalization of GFP-RelA induced by HDAC3 also did not occur in the presence of TSA. Finally, these effects of HDAC3 appeared to result from nuclear export of GFP-RelA since the addition of leptomycin B, a known inhibitor of CRM-1/exportin-1 dependent nuclear export (Yoshida, M. and Horinouchi, S., *Ann. N.Y. Acad. Sci.* 886:23–36 (1999)), preserved the nuclear pattern of GFP-RelA epifluorescence (FIG. 3I, panel 5). These findings suggest that HDAC3 mediated deacetylation of RelA promotes its export from the nucleus to the cytoplasm.

Among the target genes activated by NF-κB is the IκBα gene. See, Sun, S. C. et al., *Science* 259:1912–1915 (1993), Brown, K. et al., *Proc. Natl. Acad. Sci. USA* 90:2532–2536 (1993), and Beg, A. A. et al., *Mol. Cell. Biol.* 13:3301–3310 (1993). The resultant de novo synthesis of IκBα serves to replenish the intracellular stores of this inhibitor that were depleted during NF-κB activation. IκBα also displays nucleocytoplasmic shuttling properties and likely retrieves nuclear NF-κB complexes thereby contributing to the termination of the NF-κB transcriptional response (Arenzana-Seisdedos, F. et al., *Mol. Cell. Biol.* 15:2689–2696 (1995) and Arenzana-Seisdedos, F. et al., *J. Cell Sci.* 110:369–378 (1997)).

Example 5

IκBα is Required for the Nuclear Export of Deacetylated Forms of RelA

In view of the above findings, it was investigated whether the acetylation status of RelA regulates its assembly with IκBα (FIG. 4A). 293T cells were co-transfected with T7-RelA, p300, and HDAC3 expression vector DNA as indicated. 24 hours later, whole cell lysates were prepared and 50 µl of each of these lysates were incubated with GST-IκBα (1.0 µg). The levels of RelA captured by the GST-IκBα matrix under each condition were assessed by immunoblotting with anti-T7 antibodies (FIG. 4A, upper panel). The total amounts of GST-IκBα and RelA present in the reaction mixtures are shown in the lower two panels. Note with increasing amounts of co-transfected p300 promoting RelA acetylation that GST-IκBα bound progressively smaller amounts of RelA (compare lanes 3 and 4 to lane 2). However, when HDAC3 was co-expressed, increased dose-related binding of RelA to GST-IκBα was observed (lanes 5 and 6).

Acetylation of RelA induced by the co-expression of increasing amounts of p300 was associated with markedly diminished binding of RelA to GST-IκBα matrices (FIG. 4A, lanes 3 and 4). However, co-expression of increasing amounts HDAC3 in the presence of p300 restored RelA binding to GST-IκBα (FIG. 4A, lanes 5 and 6). Immunoblotting of the T7-RelA proteins with anti-acetylated lysine antibodies confirmed dose-related increases in RelA acetylation by p300 in lanes 3 and 4 and dose-related deacetylation of RelA by HDAC3 in lanes 5 and 6 (data not shown). These findings suggest that deacetylation of RelA by HDAC3 stimulates IκBα association.

To test whether the HDA3-induced nuclear export of RelA is dependent on IκBα, we studied the subcellular localization of GFP-RelA in murine embryo fibroblasts (MEFs) isolated from wild type or IκBα$^{-/-}$ mice produced by gene targeted disruption (FIG. 4B). See, Klement, J. F. et al., *Mol. Cell. Biol.* 16:2341–2349 (1996).

In the wild-type MEFs, GFP-RelA alone was principally expressed in the nucleus (FIG. 4B, panel 1) while co-expression of HDAC3 induced a cytoplasmic pattern of GFP-RelA epifluorescence (FIG. 4B, panel 2). MEFs were isolated from wild type animals (panels 1, 2) or gene targeted mice lacking IκBα expression (IκBα$^{-/-}$). These cells were transfected with GFP-RelA (0.3 µg) or GFP-RelA (0.3 µg) and HDAC3 (1.7 µg) expression vector DNA. Note in the IκBα$^{-/-}$ MEF cells that GFP-RelA remained nuclear in the presence of HDAC3 (panel 4) while in identically transfected wild-type MEFs, HDAC3 expression induced a cytoplasmic pattern of GFP-Rel epifluorescence (panel 2). Reconstitution of the IκBα$^{-/-}$ MEFs with limited amounts of IκBα protein by co-transfection of small quantities of an IκBα expression vector (0.1 g) produced HDAC3 dependent nuclear export of GFP-RelA (see panels 5 and 6). Numbers shown in the lower left corner of each panel represent the percentage of cells displaying the depicted phenotype derived from inspection of at least 120 cells present in multiple microscopic fields. These findings recapitulated the earlier results found in HeLa cells (FIG. 3I).

However, a very different pattern was obtained in the IκBα$^{-/-}$ MEFs. While GFP-RelA expressed alone exhibited a nuclear pattern of epifluorescence, the co-expression of HDAC3 in these IκBα$^{-/-}$ MEFs failed to induce a cytoplasmic pattern of epifluorescence (FIG. 4B, panel 4). However when IκBα expression was reconstituted in these IκBα$^{-/-}$ cells by transfection by small quantities on an IκBα expression vector, HDAC3 then induced cytoplasmic expression of the GFP-RelA protein (FIG. 4B, panel 6). In the absence of HDAC3, GFP-RelA remained principally nuclear indicating that the levels of IκBα expressed were not sufficient on their own to produce cytoplasmic sequestration in these IκBα$^{-/-}$ MEFs (FIG. 4B, panel 5). These results indicate that IκBα is required for the nuclear export of deacetylated forms of RelA, which display increased binding of IκBα.

In summary, these findings reveal a new mechanism involving reversible acetylation through which nuclear NF-κB function is regulated (FIG. 4C). RelA is subject to stimulus-coupled acetylation likely mediated through the p300 and CBP coactivators. One biological consequence of this modification is that acetylated RelA becomes a very poor substrate for binding by newly synthesized IκBα proteins whose expression is upregulated by NF-κB. These IκBα proteins also shuttle in and out of the nucleus allowing potential access to nuclear NF-κB. Our studies now identify acetylated RelA as a novel non-histone substrate of HDAC3. The deacetylation of RelA by HDAC3 promotes efficient IκBα binding by RelA.

IκBα in turn mediates the nuclear export of these RelA containing complexes, presumably reflecting the action of a leptomycin B sensitive nuclear export signal present in this inhibitor. As such, HDAC3 mediated deacetylation functions as an intranuclear molecular switch that when activated initiates a series of events culminating in the termination of the NF-κB transcriptional response. The IκBα dependent nuclear export of the HDAC3 deacetylated RelA containing complexes also serves to replenish the depleted cytoplasmic pool of latent NF-κB-IκBα complexes needed for the response of cells to the next NF-κB-inducing stimulus. This deacetylation controlled response thus both leads to the termination of the NF-κB transcriptional response and aids in reestablishing latent cytoplasmic forms of NF-κB bound to IκBα in preparation for response to the next NF-κB inducing stimulus.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method for identifying an agent that modulates NF-κB activity in transcription of a gene in a eukaryotic cell, the method comprising:
    contacting a candidate agent with a eukaryotic cell in vitro, wherein the eukaryotic cell comprises detectably labeled RelA, wherein deacetylation results in release of detectable label from RelA; and
    detecting the level of detectably labeled RelA;
    wherein detection of a decrease in the level of detectably labeled RelA in the presence of the candidate agent compared to a level of detectably labeled RelA in the absence of the candidate agent indicates that the agent inhibits activity of NF-κB gene transcription in the eukaryotic cell.

2. The method of claim 1, wherein said detecting is performed in the presence of histone deacetylase 3 (HDAC3).

3. The method of claim 1, wherein said contacting is in the presence of a protein or protein complex that acetylates RelA.

4. The method of claim 3, wherein the protein that acetylates RelA is CBP or p300.

5. The method of claim 1, wherein RelA is within a eukaryotic cell, which cell contains CBP and p300.

6. The method of claim 1, wherein said contacting is in the presence of HDAC3.

7. A method for identifying a substance that inhibits NF-κB activity, comprising testing a substance for activity in promoting deacetylation of RelA or inhibiting RelA acetylation, the method comprising the steps of:
    exposing a sample comprising a detectably labeled RelA to a test substance, wherein deacetylation results in release of detectable label from RelA;
    comparing the level of detectably labeled RelA in the sample comprising the test substance to the level of detectably labeled RelA in a sample without the test substance; and
    determining whether the level of detectably labeled RelA in the sample exposed to the test substance is less than the level of detectably labeled RelA in the sample without the test substance;
    wherein a decrease in detectably labeled RelA in the presence of the test substance indicates the test substance inhibits NF-κB activity.

8. The method according to claim 7, wherein the exposing step includes using an extract of cells, which were treated with an inducer for NF-κB activation, or a fraction of said extract.

9. The method according to claim 7, wherein a cell-free system is used for the exposing step.

10. The method according to claim 9, wherein RelA is bound to a support.

11. The method of claim 8, wherein the extract comprises p300 and CBP.

12. The method of claim 11, wherein the extract comprises HDAC3.

13. A method for identifying an agent that modulates NF-κB activity in transcription of a gene in a eukaryotic cell, the method comprising:
contacting a candidate agent with a eukaryotic cell in vitro,
immunoprecipitating a cell lysate of the eukaryotic cell to immunoprecipitate RelA; and
contacting the immunoprecipitated RelA with an anti-acetylated lysine antibody that binds acetylated RelA to detect a level of acetylated RelA,
wherein detection of a decrease in the level of acetylated RelA in the presence of the candidate agent compared to a level of acetylated RelA in the absence of the candidate agent indicates that the agent inhibits activity of NF-κB in gene transcription in the eukaryotic cell.

14. The method of claim 13, wherein the eukaryotic cell comprises a recombinant nucleic acid comprising a nucleotide sequence encoding T7-RelA, and wherein the immunoprecipitating is done using an anti-T7 antibody.

15. The method of claim 13, wherein said detecting is performed in the presence of histone deacetylase 3 (HDAC3).

16. The method of claim 13, wherein said contacting is in the presence of a protein or protein complex that acetylates RelA.

17. The method of claim 16, wherein the protein that acetylates RelA is CBP or p300.

18. The method of claim 13, wherein the eukaryotic cell comprises CBP and p300.

* * * * *

SEQUENCE LISTING

```
<160> NUMBER OF SEQ ID NOS: 3

<210> SEQ ID NO 1
<211> LENGTH: 10
<212> TYPE: DNA
<213> ORGANISM: Homo sapiens

<400> SEQUENCE: 1
gggactttcc                                                          10

<210> SEQ ID NO 2
<211> LENGTH: 10
<212> TYPE: DNA
<213> ORGANISM: Homo sapiens
<220> FEATURE:
<221> NAME/KEY: misc_feature
<222> LOCATION: (1)...(10)
<223> OTHER INFORMATION: N = A, T,G, or C

<400> SEQUENCE: 2 gggrnntycc                                                          10

<210> SEQ ID NO 3
<211> LENGTH: 22
<212> TYPE: DNA
<213> ORGANISM: Artificial Sequence
<220> FEATURE:
<223> OTHER INFORMATION: Consensus kappaB enhancer oligonucleotide

<400> SEQUENCE: 3
agttgagggg actttcccag gc                                            22
```